United States Patent
Tokai et al.

(10) Patent No.: US 7,410,987 B2
(45) Date of Patent: *Aug. 12, 2008

(54) METHOD FOR TREATING PAIN OR PRURITIS BY ADMINISTERING κ-OPIOID RECEPTOR AGONIST COMPRISING 2-PHENYLBENZOTHIAZOLINE DERIVATIVE

(75) Inventors: Maki Tokai, Osaka (JP); Takahiro Honda, Osaka (JP); Masashi Niwa, Osaka (JP); Yaeko Osumi, Osaka (JP); Ken-ichi Fujimura, Osaka (JP); Shin-ichi Kohno, Ashiya (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/434,028

(22) Filed: May 15, 2006

(65) Prior Publication Data
US 2006/0205796 A1   Sep. 14, 2006

Related U.S. Application Data

(63) Continuation of application No. 10/509,549, filed as application No. PCT/JP03/03928 on Mar. 28, 2003, now Pat. No. 7,112,598.

(30) Foreign Application Priority Data
Mar. 29, 2002 (JP) .............................. 2002-097500

(51) Int. Cl.
*A61K 31/428* (2006.01)
*A61P 29/00* (2006.01)
(52) U.S. Cl. .................................... 514/367
(58) Field of Classification Search ................. 514/367
See application file for complete search history.

(56) References Cited

U.S. PATENT DOCUMENTS

| 4,479,949 A | 10/1984 | Iwao et al. |
| 4,547,513 A | 10/1985 | Iwao et al. |
| 6,174,891 B1 | 1/2001 | Nagase et al. |

FOREIGN PATENT DOCUMENTS

| JP | 58-46079 A | 3/1983 |
| JP | 59-67276 A | 4/1984 |
| JP | 60-139679 A | 7/1985 |
| JP | 61-83175 A | 4/1986 |
| JP | 62-221679 A | 9/1987 |
| JP | 62-221680 A | 9/1987 |
| JP | 8-231399 A | 9/1996 |
| WO | WO 98/23290 A1 | 6/1998 |

OTHER PUBLICATIONS

Prado, W.A., Database Medline on STN, "Involvement of Caclium in Pain and Antinociception", PubMed ID 112854555, Jun. 7, 2001.*
Chen et al., Chemical Abstracts, 145:502582, 2006.*
Vanegas et al., Pain, 85, 9-18 (2000).*
Yamamoto, K. et al., "Novel Calcium Antagonists, Synthesis and Structure-Activity Relationship Studies of Benzothiazoline Derivatives"; J. Med. Chem., (1988), 31, 919-930.
Fujita, M. et al., "Synthesis and Calcium Antagonist Activity of (+)-(R)- and (−) (S)-3-Acetyl-2-[5-methoxy-2-[4-[N-methyl-N-(3,4,5-trimethoxyphenethyl)amino]butoxy]-phenyl]benzothiazoline Hydrochloride", Chem. Pharm. Bull., (1990), 38(4), 936-941.
Way, E.L., "Review of Revues", Annu. Rev. Pharmacol. Toxicol., (1992), 32, 9-23.
"Experimental Medicine", 18 (17), 2332-2337 (2000).
Satoh, Masamichi, "Molecular Neuropharmacology of Nociceptive Transmission and Opioid Receptors", J. Pharm. Soc., 120 (12), 1291-1307, (2000).
"All of Opinoid", published by Mikusu Co., Ltd., pp. 222-229, (1999).
"All of Opinoid", published by Mikusu Co., Ltd., pp. 25-36, (1999).

* cited by examiner

*Primary Examiner*—Fiona T Powers
(74) *Attorney, Agent, or Firm*—Frishauf, Holtz, Goodman & Chick, P.C.

(57) ABSTRACT

A method of treating pain or pruritis comprising administering to a patient in need thereof a pharmaceutically effective amount of a κ opioid receptor agonist of the formula

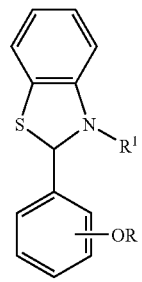

wherein R is an alkyl having an amino group as a substituent; and $R^1$ is acyl.

14 Claims, No Drawings

METHOD FOR TREATING PAIN OR PRURITIS BY ADMINISTERING κ-OPIOID RECEPTOR AGONIST COMPRISING 2-PHENYLBENZOTHIAZOLINE DERIVATIVE

CROSS-REFERENCE TO RELATED APPLICATIONS

This application is a continuation application of Ser. No. 10/509,549 filed Sep. 28, 2004 (U.S. Pat. No. 7,112,598), which is the United States national phase application of International Application PCT/JP03/03928 filed Mar. 28, 2003.

TECHNICAL FIELD

The present invention relates to κ opioid receptor agonists comprising 2-phenylbenzothiazoline derivatives or salts thereof and novel 2-phenylbenzothiazoline derivatives or salts thereof. The κ opioid receptor agonists of the present invention are particularly useful as therapeutic agents for pain, pruritus and the like.

BACKGROUND ART

Pain plays a physiologically important role as a warning reaction to know danger. On the other hand, pain is also a significant cause to lower quality of lives (QOL) of patients. Pain accompanying almost all diseases typified by rheumatic diseases is one of causes of dysfunction. Accordingly, it is medically very important to control pain (Experimental Medicine, 18 (17), 2332-2337 (2000) and J. Pharm. Soc., 120 (12), 1291-1307 (2000)).

Narcotic analgesics such as morphine and nonnarcotic analgesics such as non-steroidal anti-inflammatory drugs (NSAIDs), indometacin and diclofenac sodium, are widely used now as drugs which control pain.

However, while the narcotic analgesics have strong analgesic actions, they have side effects such as drug dependence, and their use are strictly limited accordingly. On the other hand, NSAIDs are very useful as therapeutic agents for pain derived from synthesis of inflammatory mediators such as prostaglandin but have no strong analgesic actions unlike the narcotic analgesics.

In recent years, μ (mu), κ (kappa) and δ (delta) receptors have been proposed as subtypes of the opioid receptors, and it has been clarified that the side effects such as drug dependence of morphine are exhibited through the κ opioid receptor. Further, it has been found that analgesic actions are exhibited through any of the μ opioid receptor, the κ opioid receptor and the δ opioid receptor.

These findings suggest a possibility that drugs which selectively act on the κ opioid receptor and the δ opioid receptor can be analgesics which solve problems of drugs which act on the μ opioid receptor.

Compounds reported to serve as drugs which selectively act on the κ opioid receptor are compounds having a phenylacetic amide skeleton represented by U50488H, compounds having a benzodiazepine skeleton represented by Thifuadom, compounds having a phenothiazine skeleton represented by Apadoline, compounds having a 4,5-epoxymorphinan skeleton represented by TRK-820 and the like ("All of opioid", published by Mikusu Co., Ltd., p. 222-229 (1999)).

It is known that pain is weaken by activating the κ opioid receptor, and it was reported that a κ opioid receptor agonist is useful as an analgesic ("All of opioid", published by Mikusu Co., Ltd., p. 25-36 (1999)). Further, it was also reported that the κ opioid receptor agonist has an antipruritic action (WO 98/23290).

On the other hand, Japanese Laid-open Patent Publication Nos. 46079/1983, 67276/1984, 139679/1985 and 221679/1987 reported that 2-phenylbenzothiazoline derivatives have calcium antagonism and platelet aggregation actions and are useful as therapeutic agents for cardiovascular diseases such as hypertension, thrombosis, angina and arrhythmia.

However, actions of these 2-phenylbenzothiazoline derivatives on the κ opioid receptor are not known, much less it is impossible to presume which derivatives thereof act as agonists or antagonists at all. Their analgesic actions and antipruritic actions are not reported at all, either.

It is very interesting subjects to find new pharmacological actions of the known 2-phenylbenzothiazoline derivatives, which are useful as pharmaceuticals, and further to synthesize novel 2-phenylbenzothiazoline derivatives, which are their analogs, and to find useful pharmacological actions thereof.

DISCLOSURE OF THE INVENTION

Conducting intensive study in order to find new pharmacological actions of 2-phenylbenzothiazoline derivatives, the present inventors found that 2-phenylbenzothiazoline derivatives have excellent agonist actions on a human κ opioid receptor and are useful as therapeutic agents for pain and pruritus. Further, the present inventors prepared many novel 2-phenylbenzothiazoline derivatives wherein new various substituents such as hydroxyl, alkoxy and -A$_2$-R$^6$ were introduced to a nitrogen atom of an aminoalkylene group and found that these derivatives also have the κ opioid receptor agonist actions. Thus the present invention has been accomplished.

The present invention relates to κ opioid receptor agonists comprising compounds having the chemical structure represented by the general formula [I] as a basic skeleton or salts thereof. To exhibit κ opioid receptor agonist actions, it is important to have an alkyl group having an amino group as a substituent at a phenyl group of 2-phenylbenzothiazoline and to have an acyl group at a nitrogen atom of 2-phenylbenzothiazoline.

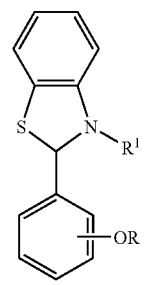

[I]

[wherein R is alkyl having the amino group as the substituent; and R$^1$ is acyl.]

More specifically, the present invention relates to κ opioid receptor agonists comprising compounds represented by the general formula [II] or salts thereof.

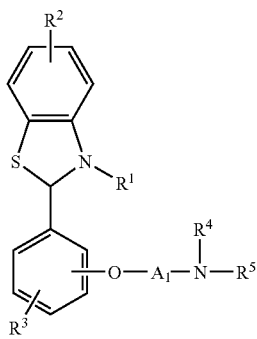

[wherein R¹ is acyl;
R² and R³, the same or different, are hydrogen, halogen, alkyl, cycloalkyl, aryl, hydroxyl or esters thereof, alkoxy, aryloxy, carboxyl or esters thereof, alkylcarbonyl, arylcarbonyl, amino, alkylamino, arylamino, cyano or nitro, wherein the alkyl, cycloalkyl, aryl, alkoxy, aryloxy, alkylcarbonyl, arylcarbonyl, alkylamino or arylamino can be substituted by halogen, alkyl, cycloalkyl, aryl, hydroxyl or an ester thereof, alkoxy, aryloxy, carboxyl or an ester thereof, alkylcarbonyl, arylcarbonyl, amino, alkylamino, arylamino, cyano or nitro;
R⁴ and R⁵, the same or different, are hydrogen, alkyl, cycloalkyl, aryl, hydroxyl or esters thereof, alkoxy, aryloxy or acyl, wherein the alkyl, cycloalkyl, aryl, alkoxy, aryloxy or acyl can be substituted by halogen, alkyl, cycloalkyl, aryl, hydroxyl or an ester thereof, alkoxy, aryloxy, carboxyl or an ester, thereof, alkylcarbonyl, arylcarbonyl, amino, alkylamino, arylamino, mercapto, alkylthio, arylthio, cyano, nitro or a heterocycle, and further the alkyl, cycloalkyl, aryl, alkoxy, aryloxy, alkylcarbonyl, arylcarbonyl, alkylamino, arylamino, alkylthio, arylthio or heterocycle can be substituted by aryl, hydroxyl or an ester thereof, alkoxy, aryloxy, alkoxyalkoxy or carboxyl or an ester thereof;
R⁴ and R⁵ can be bonded each other to form a heterocycle, the heterocycle can be substituted by halogen, alkyl, cycloalkyl, aryl, hydroxyl or an ester thereof, alkoxy, aryloxy or carboxyl or an ester thereof, and further the alkyl, cycloalkyl, aryl, alkoxy or aryloxy can be substituted by aryl, hydroxyl or an ester thereof, alkoxy, aryloxy, alkoxyalkoxy or carboxyl or an ester thereof; and
A₁ is alkylene.]

Compounds represented by the general formula [III] are novel compounds which are unknown in literatures among the compounds represented by the general formulae [I] and [II].

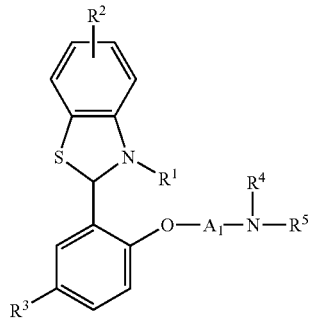

[wherein R¹ is acyl:

R² is hydrogen, halogen or alkyl, wherein the alkyl can be substituted by halogen;
R³ is halogen or alkoxy;
R⁴ is alkyl or cycloalkyl, wherein the alkyl can be substituted by cycloalkyl, aryl, hydroxyl or an ester thereof or alkoxy;
R⁴ and R⁵ can be bonded each other to form a pyrrolidine ring substituted by hydroxyl or an ester thereof, alkoxy or alkoxyalkyl;
R⁵ is hydroxyl or an ester thereof, alkoxy or -A₂-R⁶;
R⁶ is hydroxyl or an ester thereof, alkoxy, alkoxyalkoxy, alkoxyalkoxyalkoxy, mercapto or alkylthio; and
A₁ and A₂, the same or different, are alkylene.

Provided that when R⁴ and R⁵ are bonded each other to form the pyrrolidine ring substituted by hydroxyl or the ester thereof, R² is halogen, when R⁴ and R⁵ are bonded each other to form the pyrrolidine ring substituted by alkoxyalkyl, R² is hydrogen, when R⁶ is hydroxyl or the ester thereof, R⁴ is isopropyl.]

The respective groups defined above are described in detail below.

The alkyl having the amino group as the substituent is alkyl having a substituted or unsubstituted amino group as the substituent and is more specifically a group represented by the following general formula [II].

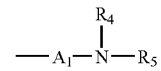

The alkyl is straight-chain or branched alkyl having one to six carbon atoms such as methyl, ethyl, n-propyl, isopropyl, n-butyl, isobutyl, s-butyl, tert-butyl, n-pentyl, isopentyl or n-hexyl.

The acyl is a partial structure such as hydrocarbonyl, alkylcarbonyl or arylcarbonyl of substituted or unsubstituted carboxylic acids and is acyl having one to 12 carbon atoms such as formyl, acetyl, propionyl, butyryl, isobutyryl valeryl, isovaleryl, pivaloyl, monochloroacetyl, trichloroacetyl, trifluoroacetyl or benzoyl.

The halogen is fluorine, chlorine, bromine or iodine.

The cycloalkyl is cyclic cycloalkyl having three to eight carbon atoms such as cyclopropyl, cyclobutyl, cyclopentyl, cyclohexyl, cycloheptyl or cyclooctyl.

The aryl is a monocyclic aromatic hydrocarbon group such as phenyl, tolyl, xylyl or mesityl and a condensed-ring aromatic hydrocarbon group such as indenyl, naphthyl, phenanthryl, anthryl or pyrenyl.

The alkoxy is straight-chain or branched alkoxy having one to six carbon atoms such as methoxy, ethoxy, n-propoxy, isopropoxy, n-butoxy, isobutoxy, s-butoxy, tert-butoxy, n-pentoxy, isopentoxy or n-hexyloxy.

The heterocycle is a saturated or unsaturated monocyclic or condensed polycyclic heterocycle having one to four the same or different nitrogen atom(s), oxygen atom(s) or sulfur atom(s) in its ring.

Specific examples of saturated monocyclic heterocycles are pyrrolidine, piperidine, homopiperidine, piperazine and the like having a nitrogen atom in its ring; tetrahydrofuran, tetrahydropyran and the like having an oxygen atom in its ring; tetrahydrothiophene and tetrahydrothiopyran and the like having a sulfur atom in its ring; morpholine and the like having a nitrogen atom and an oxygen atom in its ring; and thiomorpholine and the like having a nitrogen atom and a sulfur atom in its ring.

The saturated monocyclic heterocycle can be condensed with a benzene ring or the like to form a condensed polycyclic heterocycle such as tetrahydroquinoline or tetrahydroisoquinoline.

Specific examples of unsaturated monocyclic heterocycles are pyridine, pyrimidine, pyrrole, imidazole and the like having a nitrogen atom in its ring; furan and the like having an oxygen in its ring; thiophene and the like having a sulfur atom in its ring; oxazole and the like having a nitrogen atom and an oxygen atom in its ring; and thiazole and the like having a nitrogen atom and a sulfur atom in its ring.

The unsaturated monocyclic heterocycle can be condensed with a benzene ring or the like to form a condensed polycyclic heterocycle such as indole, quinoline, phenanthridine, benzimidazole, benzoxazole or benzothiazole.

The alkylene is straight-chain or branched alkylene having one to six carbon atoms such as methylene, ethylene, trimethylene, tetramethylene, pentamethylene, hexamethylene, methylmethylene, dimethylmethylene, ethylmethylene, propylmethylene, isopropylmethylene, butylmethylene, isobutylmethylene, s-butylmethylene, tert-butylmethylene, dimethylethylene, ethylethylene, propylethylene, isopropylethylene or methyltrimethylene.

The compounds represented by the general formula [I], more specifically the compounds represented by the general formula [II] are hereinafter referred to as "the present compounds" as far as there is no proviso.

The ester of hydroxyl is an ester with an alkylcarboxylic acid, an arylcarboxylic acid or the like. Examples of alkylcarboxylic acids are acetic acid, propionic acid, butyric acid, valeric acid, 2,2-dimethylpropanoic acid and the like, and examples of arylcarboxylic acids are benzoic acid, toluic acid and the like.

The ester of carboxyl is an ester with an alkyl alcohol, an aryl alcohol or the like. Examples of alkyl alcohols are methanol, ethanol, propanol, butanol and the like, and examples of aryl alcohols are phenol, cresol, naphthol and the like.

When the present compound has carboxyl as a substituent, the carboxyl can form an amide with an alkylamine, an arylamine or the like. Examples of alkylamines are methylamine, ethylamine, ethylmethylamine, dimethylamine, diethylamine and the like. Examples of arylamines are aniline, diphenylamine, ethylphenylamine and the like.

Hydroxyl, mercapto, amino, alkylamino, arylamino or a nitrogen atom of the heterocycle can be protected with a protecting group in the present compounds.

The protecting group of hydroxyl is a protecting group which is widely used as the protecting group of hydroxyl such as substituted or unsubstituted alkyl such as benzyloxymethyl, allyl, benzyl, p-methoxybenzyl, trityl, tetrahydropyranyl or tetrahydrofuranyl; substituted or unsubstituted ester such as methoxycarbonyl, ethoxycarbonyl, isobutoxycarbonyl, tert-butoxycarbonyl, vinyloxycarbonyl, allyloxycarbonyl, benzyloxycarbonyl or p-methoxybenzyloxycarbonyl; or saturated or unsaturated silyl such as trimethylsilyl, triethylsilyl, triisopropylsilyl, tert-butyldimethylsilyl or tert-butyldiphenylsilyl.

The protecting group of mercapto is a protecting group which is widely used as the protecting group of mercapto such as substituted or unsubstituted alkyl such as methoxymethyl, isobutoxymethyl, benzylthiomethyl, phenylthiomethyl, benzyl, p-methoxybenzyl, tert-butyl, trityl or tetrahydropyranyl; substituted or unsubstituted acyl such as acetyl, propionyl, butylyl, pivaloyl, benzoyl or tenoyl; substituted or unsubstituted ester such as methoxycarbonyl, tert-butoxycarbonyl or benzyloxycarbonyl; or substituted thio such as ethylthio, tert-butylthio or phenylthio.

The protecting group of amino, alkylamino, arylamino or the nitrogen atom of the heterocycle is a protecting group which is widely used as the protecting group of amino, alkylamino, arylamino or the nitrogen atom of the heterocycle such as substituted or unsubstituted alkyl such as allyl, benzyl, trityl, (4-methoxyphenyl)diphenylmethyl or diphenylmethyl; substituted or unsubstituted acyl such as formyl, acetyl, trichloroacetyl, trifluoroacetyl, picolinoyl or benzoyl; ester such as methoxycarbonyl, isobutoxycarbonyl, tert-butoxycarbonyl, 2,2,2-trichloroethoxycarbonyl, benzyloxycarbonyl, diphenylmethoxycarbonyl or phenoxycarbonyl; or substituted or unsubstituted sulfonyl such as methane sulfonyl, benzene sulfonyl, toluenesulfonyl or 2,4,6-trimethylbenzenesulfonyl.

The "salts" in the present invention can be any pharmaceutically acceptable salts and are exemplified by salts with an inorganic acid such as hydrochloric acid, hydrobromic acid, hydroiodic acid, nitric acid, sulfuric acid or phosphoric acid, salts with an organic acid such as acetic acid, fumaric acid, maleic acid, succinic acid, citric acid, tartaric acid, adipic acid, lactic acid, methanesulfonic acid, trifluoromethanesulfonic acid or p-toluenesulfonic acid, salts with an alkali metal such as lithium, sodium or potassium, salts with an alkaline earth metal such as calcium or magnesium, and quaternary salts with ammonia, methyl iodide or the like.

When there are geometrical isomers or optical isomers in the present compounds, these isomers are also included in the scope of the present invention.

Further, the present compounds can be in the form of hydrates or solvates.

Preferred examples of the present invention are the following. (1) κ opioid receptor agonist comprising compounds or salts thereof as active ingredients wherein the respective groups defined in the general formula [II] are selected from the following groups or combinations thereof, 1) $R^2$ and $R^3$, the same or different, are hydrogen, halogen, alkyl or alkoxy, wherein the alkyl can be substituted by halogen.
2) $R^4$ and $R^5$, the same or different, are hydrogen, alkyl, cycloalkyl, hydroxyl or esters thereof or alkoxy, wherein the alkyl can be substituted by alkyl, cycloalkyl, aryl, hydroxyl or an ester thereof, alkoxy, carboxyl or an ester thereof, mercapto, alkylthio or a heterocycle, and further the alkyl or alkoxy can be substituted by hydroxyl or an ester thereof, alkoxy or alkoxyalkoxy.
3) $R^4$ and $R^5$ can be bonded each other to form a pyrrolidine ring or a piperidine ring, wherein the pyrrolidine ring or piperidine ring can be substituted by alkyl, hydroxyl or an ester thereof, alkoxy or carboxyl or an ester thereof, and further the alkyl can be substituted by hydroxyl or an ester thereof or alkoxy.

κ opioid receptor agonists comprising compounds or salts thereof wherein the respective groups defined by the general formula [II] are the following groups are more preferable, $R^1$ is acyl, R² is hydrogen, halogen or alkyl, wherein the alkyl can be substituted by halogen, R³ is halogen or alkoxy, R⁴ is hydrogen, alkyl or cycloalkyl, wherein the alkyl can be substituted by alkyl, cycloalkyl, aryl, hydroxyl or an ester thereof or alkoxy, and further the alkyl can be substituted by hydroxyl or an ester thereof or alkoxy, R⁴ and R⁵ can be bonded each other to form a pyrrolidine ring or a piperidine ring, wherein the pyrrolidine ring or piperidine ring can be substituted by alkyl, hydroxyl or an ester thereof, alkoxy or carboxyl or an ester thereof, and further the alkyl can be substituted by hydroxyl or an ester thereof or alkoxy, R⁵ is alkyl, hydroxyl or an ester thereof or alkoxy, wherein the alkyl can be substituted by cycloalkyl, aryl, hydroxyl or an ester thereof, alkoxy, carboxyl or an ester thereof, mercapto, alkylthio or a heterocycle, and further the alkoxy can be substituted by hydroxyl, alkoxy or alkoxyalkoxy, and A₁ is alkylene.

κ opioid receptor agonists comprising compounds or salts thereof wherein the respective groups defined by the general formula [II] are the following groups are particularly preferable, R¹ is acyl, R² is hydrogen, halogen or alkyl, wherein the alkyl can be substituted by halogen, R³ is halogen or alkoxy, R⁴ is alkyl or cycloalkyl, wherein the alkyl can be substituted by alkyl, cycloalkyl, aryl, hydroxyl or an ester thereof or alkoxy, R⁴ and R⁵ can be bonded each other to form a pyrrolidine ring, wherein the pyrrolidine ring can be substituted by alkyl, hydroxyl or an ester thereof or alkoxy, and further the alkyl can be substituted by hydroxyl or an ester thereof or alkoxy, R⁵ is alkyl, hydroxyl or an ester thereof or alkoxy, wherein the alkyl can be substituted by hydroxyl or an ester thereof, alkoxy, mercapto or alkylthio, and further the alkoxy can be substituted by alkoxy or alkoxyalkoxy, and A₁ is alkylene.

Particularly preferred specific examples in the present invention are κ opioid receptor agonists comprising the following compounds and salts thereof.

3-Acetyl-6-chloro-2-[2-(3-(N-(2-hydroxyethyl)-N-isopropylamino)-propoxy)-5-methoxyphenyl]benzothiazoline

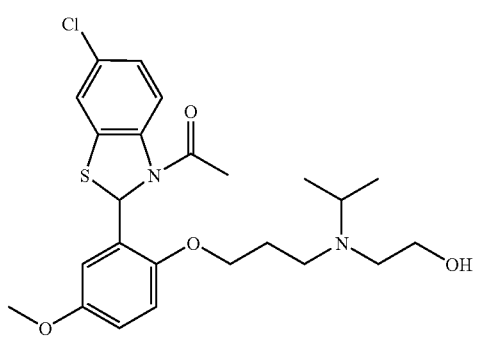

3-Acetyl-6-chloro-2-[2-(3-(N-(2-hydroxyethyl)-N-(2-methylpropyl)-amino)propoxy)-5-methoxyphenyl]benzothiazoline

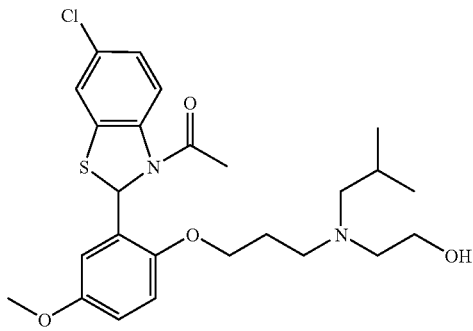

3-Acetyl-6-chloro-2-[2-(3-((2S)-2-hydroxymethylazolan-1-yl)propoxy)-5-methoxyphenyl]benzothiazoline

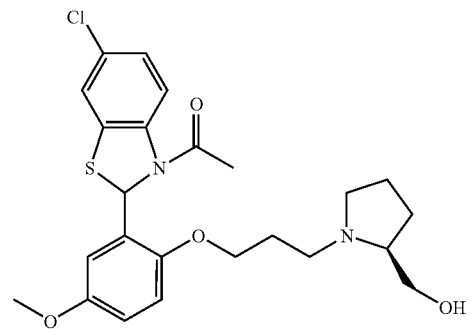

3-Acetyl-6-chloro-2-[2-(3-((3S)-hydroxyazolan-1-yl)propoxy)-5-methoxyphenyl]benzothiazoline

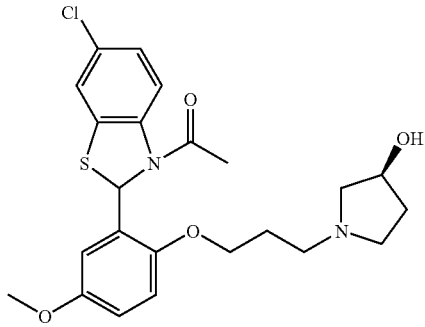

9

3-Acetyl-6-chloro-2-[2-(3-(N-isopropyl-N-(2-methoxyethyl)amino)-propoxy)-5-methoxyphenyl]benzothiazoline

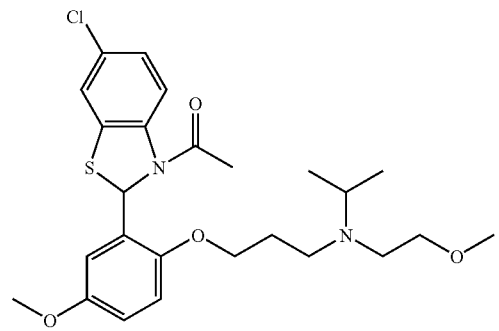

3-Acetyl-6-chloro-2-[2-(3-(N-(2-ethoxyethyl)-N-isopropylamino)-propoxy)-5-methoxyphenyl]benzothiazoline

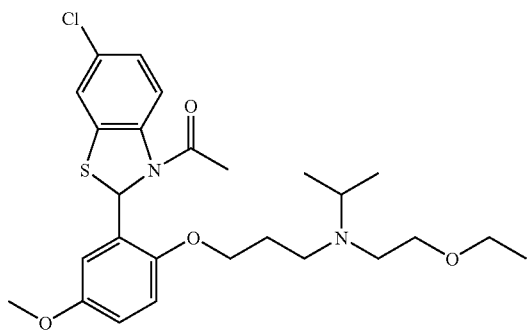

3-Acetyl-6-chloro-2-[2-(3-(N-(furan-2-ylmethyl)-N-isopropylamino)-propoxy)-5-methoxyphenyl]benzothiazoline

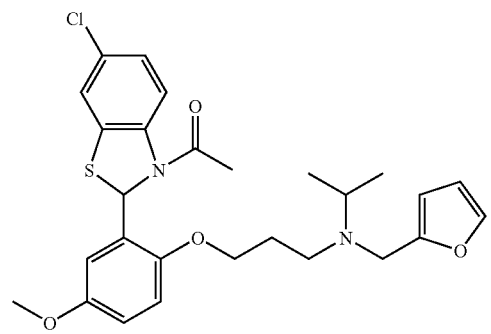

10

3-Acetyl-2-[2-(3-(N-(2-hydroxyethyl)-N-isopropylamino)propoxy)-5-methoxyphenyl]-5-trifluoromethylbenzothiazoline

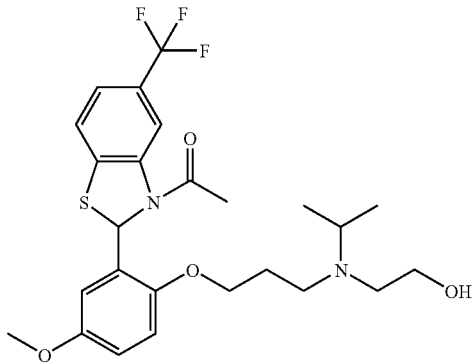

3-Acetyl-5-chloro-2-[2-(3-(N-(2-hydroxyethyl)-N-isopropylamino)-propoxy)-5-methoxyphenyl]benzothiazoline

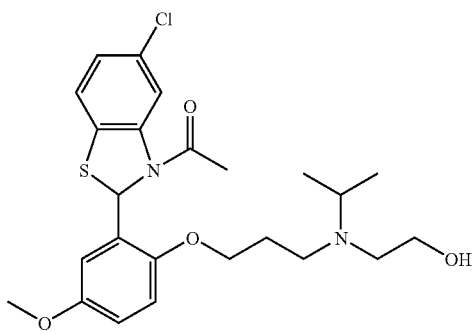

3-Acetyl-6-chloro-2-[2-(3-(N-(2-hydroxyethyl)-N-isopropylamino)-1-methylpropoxy)-5-methoxyphenyl]benzothiazoline

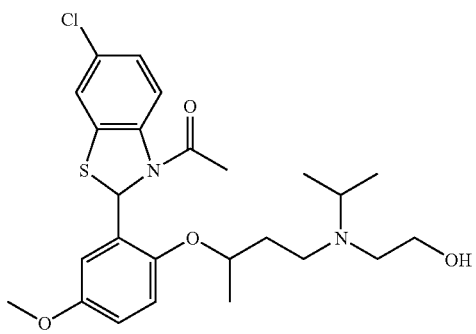

11

3-Acetyl-2-[2-(3-(N-isopropyl-N-(2-methoxyethyl)amino)propoxy)-5-methoxyphenyl]benzothiazoline

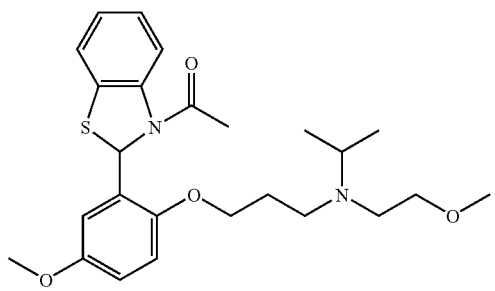

(+)-3-Acetyl-6-chloro-2-[2-(3-(N-isopropyl-N-(2-methoxyethyl)amino)-propoxy)-5-methoxyphenyl]benzothiazoline

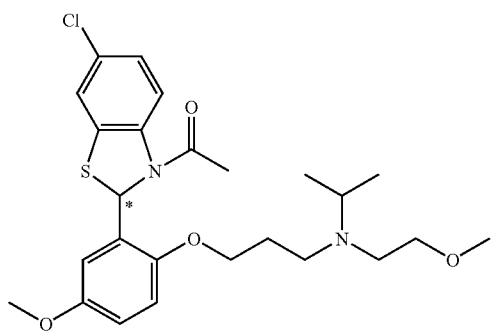

(+)-3-Acetyl-6-chloro-2-[2-(3-(N-(2-hydroxyethyl)-N-isopropylamino)-propoxy)-5-methoxyphenyl]benzothiazoline

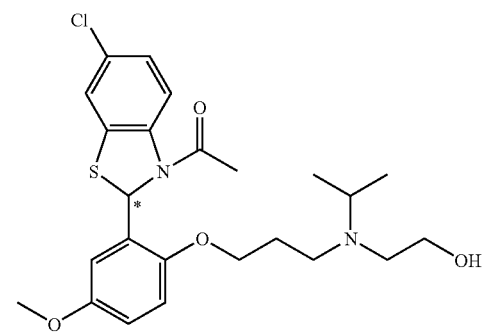

12

(+)-3-Acetyl-6-chloro-2-[2-(3-(N-(2-ethoxyethyl)-N-isopropylamino)-propoxy)-5-methoxyphenyl]benzothiazoline

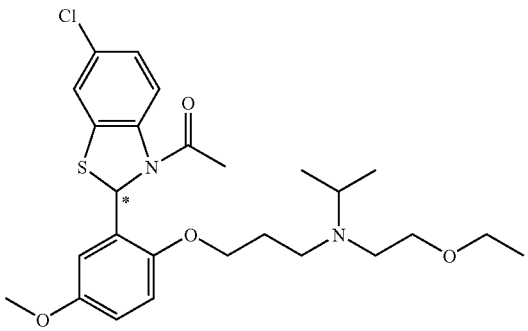

(+)-3-Acetyl-6-chloro-2-[2-(3-(N-isopropylamino-N-(thiophen-2-ylmethyl)-amino)propoxy)-5-methoxyphenyl]benzothiazoline

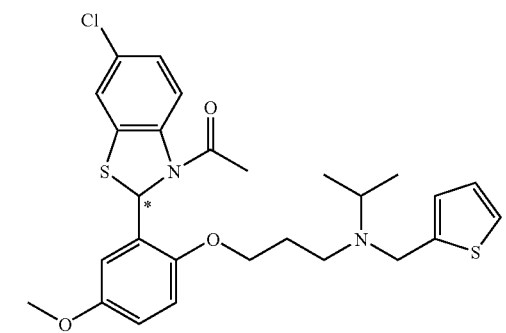

(+)-3-Acetyl-6-chloro-2-[2-(3-(N-(furan-2-ylmethyl)-N-isopropyl-amino)propoxy)-5-methoxyphenyl]benzothiazoline

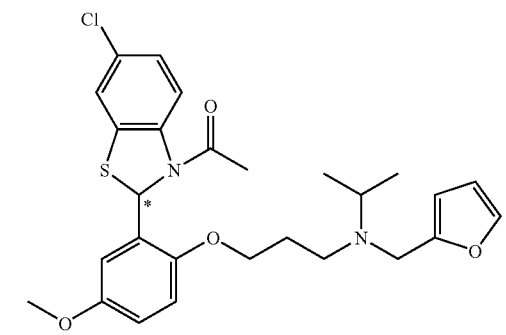

13

(+)-3-Acetyl-6-chloro-2-[2-(3-(N-ethyl-N-isopropylamino)propoxy)-5-methoxyphenyl]benzothiazoline

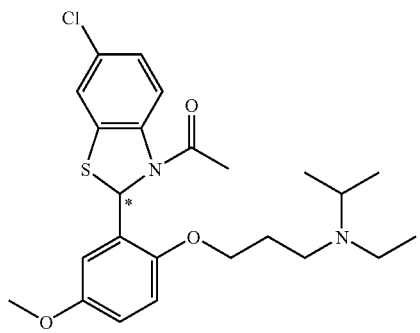

(+)-3-Acetyl-6-chloro-2-[2-(3-(N,N-diisopropylamino)propoxy)-5-methoxyphenyl]benzothiazoline

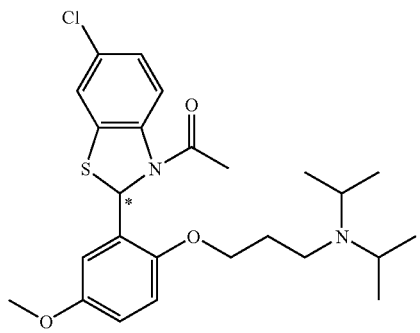

(+)-3-Acetyl-6-chloro-2-[2-(3-(N-isopropyl-N-methylamino)propoxy)-5-methoxyphenyl]benzothiazoline

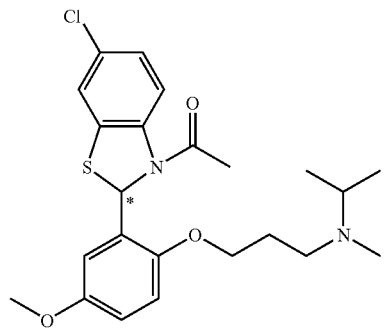

14

(+)-3-Acetyl-6-chloro-2-[2-(3-(N-(2-hydroxyethyl)-N-methylamino)-propoxy)-5-methoxyphenyl]benzothiazoline

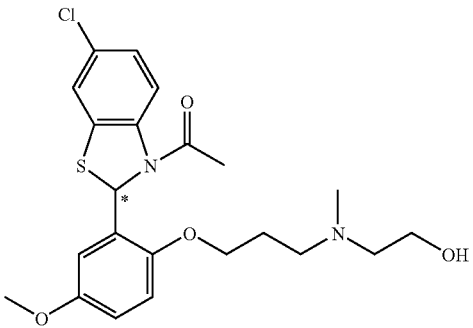

(−)-3-Acetyl-6-chloro-2-[2-(3-(N-isopropyl-N-(2-methoxyethyl)amino)-propoxy)-5-methoxyphenyl]benzothiazoline

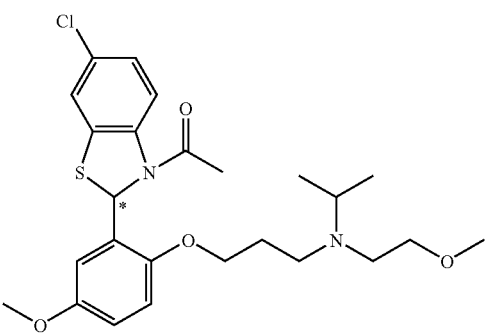

(−)-3-Acetyl-6-chloro-2-[2-(3-(N-(2-hydroxyethyl)-N-isopropylamino)-propoxy)-5-methoxyphenyl]benzothiazoline

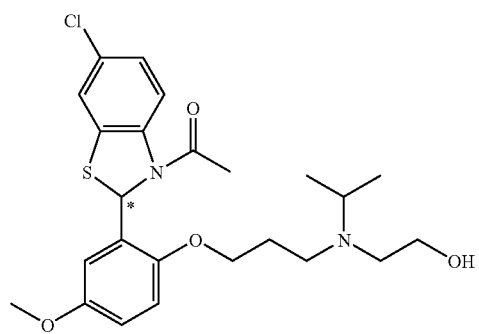

15

(−)-3-Acetyl-6-chloro-2-[2-(3-(N-(2-ethoxyethyl)-N-isopropylamino)-propoxy)-5-methoxyphenyl]benzothiazoline

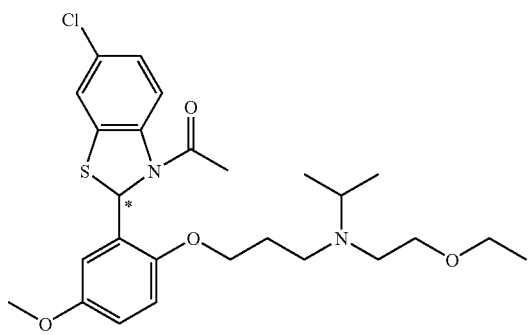

(+)-3-Acetyl-2-[2-(3-(N-(2-ethoxyethyl)-N-isopropylamino)propoxy)-5-methoxyphenyl]benzothiazoline

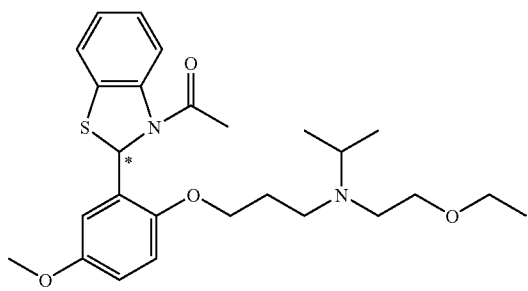

(+)-3-Acetyl-2-[2-(3-(N-(2-hydroxyethyl)-N-isopropylamino)propoxy)-5-methoxyphenyl]benzothiazoline

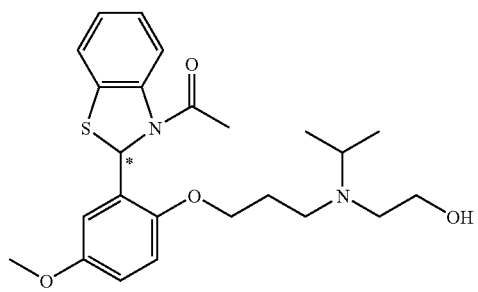

16

3-Acetyl-6-chloro-2-[2-(3-(N-isopropyl-N-(2-methoxymethyloxy-ethyl) amino)propoxy)-5-methoxyphenyl]benzothiazoline

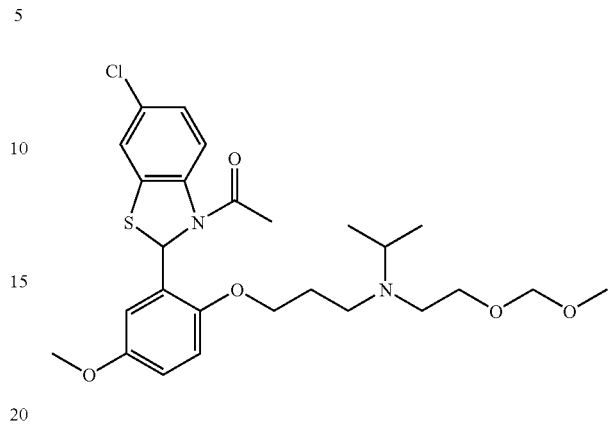

3-Acetyl-6-chloro-2-[2-(3-(N-isopropyl-N-(2-(2-methoxyethoxy-methoxy)ethyl)amino)propoxy)-5-methoxyphenyl]benzothiazoline

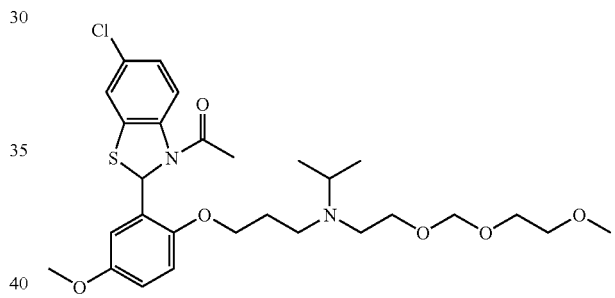

2-[2-(3-(N-(2-Acetoxyethyl)-N-isopropylamino)propoxy)-5-methoxyphenyl]-3-acetyl-6-chlorobenzothiazoline

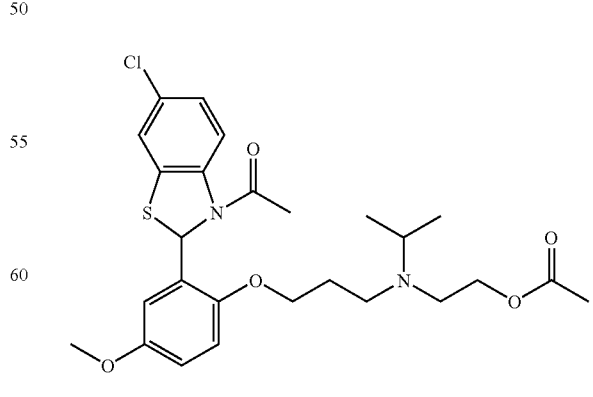

17

3-Acetyl-6-chloro-2-[2-(3-(N-isopropyl-N-(2-phenylcarboxyethyl)-amino) propoxy)-5-methoxyphenyl]benzothiazoline

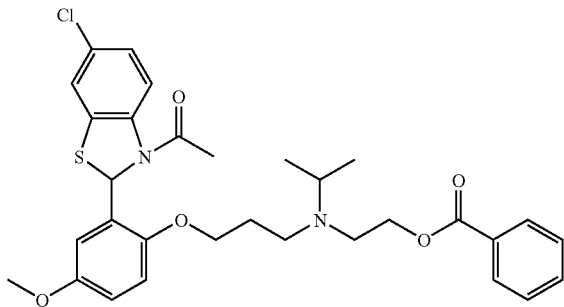

3-Acetyl-6-chloro-2-[2-(3-(N-hydroxy-N-isopropylamino)propoxy)-5-methoxyphenyl]benzothiazoline

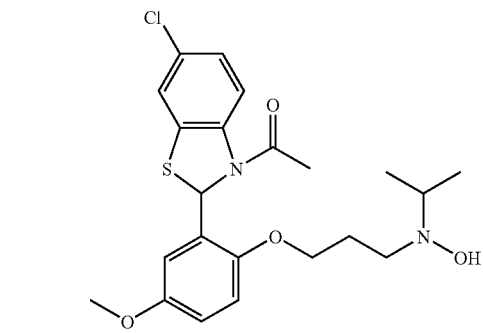

3-Acetyl-6-chloro-2-[2-(3-(N-cyclohexyl-N-(2-hydroxyethyl)amino)-propoxy)-5-methoxyphenyl]benzothiazoline

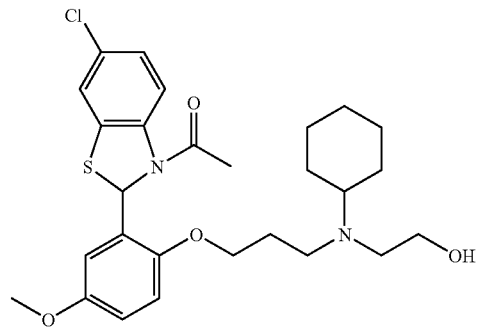

18

3-Acetyl-6-chloro-2-[2-(3-(N-ethyl-N-(2-hydroxyethyl)amino)propoxy)-5-methoxyphenyl]benzothiazoline

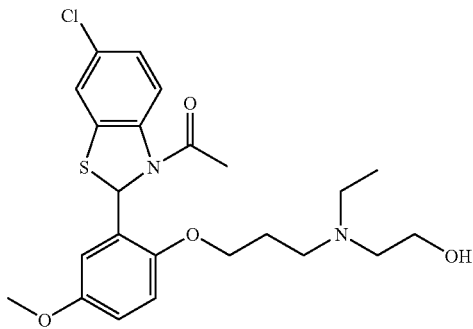

3-Acetyl-2-[2-(3-(N-(2-ethoxyethyl)-N-isopropylamino)propoxy)-5-methoxyphenyl]benzothiazoline

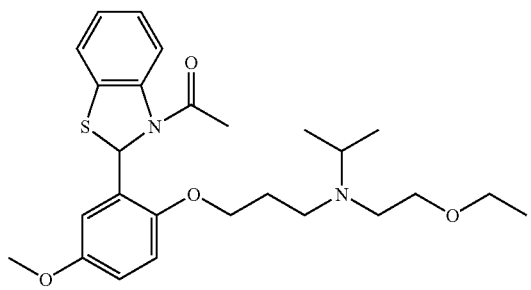

(+)-3-Acetyl-2-[2-(3-(N-isopropyl-N-(2-methoxyethyl)amino)propoxy)-5-methoxyphenyl]benzothiazoline

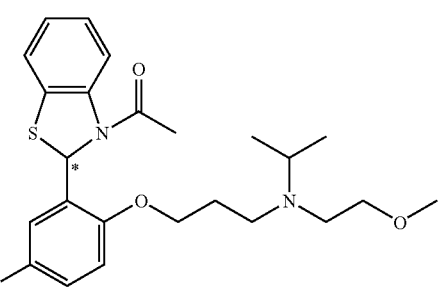

Preferred examples of compounds represented by the formula [III] are the following.

(1) Compounds or salts thereof wherein the respective groups defined by the general formula [III] are the following groups, R¹ is acyl,
R² is hydrogen,
R³ is alkoxy,
R⁴ is alkyl,
R⁴ and R⁵ can be bonded each other to form a pyrrolidine ring substituted by alkoxy or alkoxyalkyl,
R⁵ is hydroxyl or an ester thereof, alkoxy or -A₂-R⁶,
R⁶ is alkoxy, alkoxyalkoxy or alkoxyalkoxyalkoxy, and
A₁ and A₂, the same or different, are alkylene.

(2) Compounds or salts thereof wherein the respective groups defined by the general formula [III] are the following groups,
R¹ is acyl,
R² is halogen,
R³ is alkoxy,
R⁴ is alkyl,
R⁴ and R⁵ can be bonded each other to form a pyrrolidine ring substituted by hydroxyl or an ester thereof or alkoxy,
R⁵ is hydroxyl or an ester thereof, alkoxy or -A₂-R⁶,
R⁶ is alkoxy, alkoxyalkoxy or alkoxyalkoxyalkoxy, and
A₁ and A₂, the same or different, are alkylene.

(3) Compounds or salts thereof wherein the respective groups defined by the general formula [III] are the following groups,
R¹ is acyl,
R² is hydrogen or halogen,
R³ is alkoxy,
R⁴ is isopropyl,
R⁵ is -A₂-R⁶,
R⁶ is hydroxyl or an ester thereof, and
A₁ and A₂, the same or different, are alkylene.

Particularly preferred specific examples of compounds represented by the formula [III] are the following compounds and salts thereof.

3-Acetyl-6-chloro-2-[2-(3-(N-(2-hydroxyethyl)-N-isopropylamino)-propoxy)-5-methoxyphenyl]benzothiazoline 3-Acetyl-6-chloro-2-[2-(3-(N-hydroxy-N-isopropylamino)propoxy)-5-methoxyphenyl]benzothiazoline

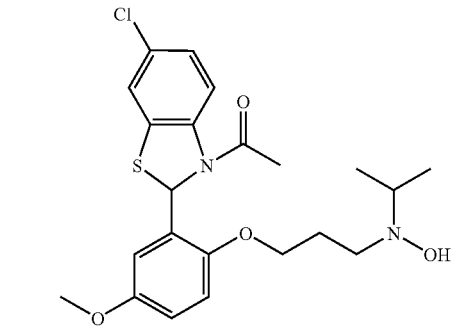

3-Acetyl-6-chloro-2-[2-(3-(N-isopropyl-N-(2-methoxyethyl)amino)-propoxy)-5-methoxyphenyl]benzothiazoline

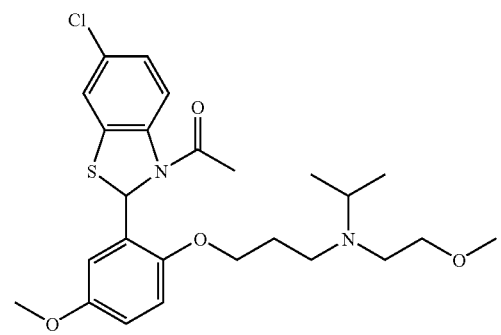

3-Acetyl-6-chloro-2-[2-(3-(N-(2-ethoxyethyl)-N-isopropylamino)-propoxy)-5-methoxyphenyl]benzothiazoline

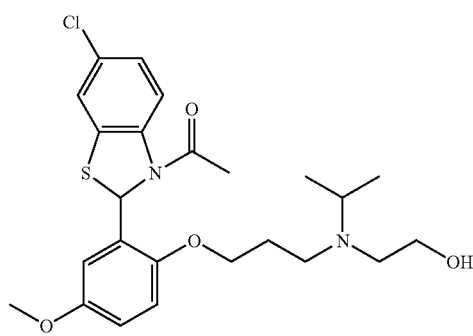

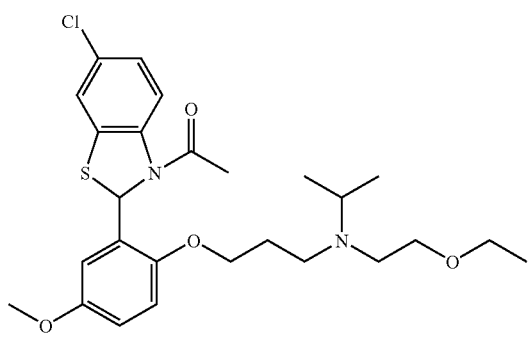

21

3-Acetyl-5-chloro-2-[2-(3-(N-(2-hydroxyethyl)-N-isopropylamino)-propoxy)-5-methoxyphenyl]benzothiazoline

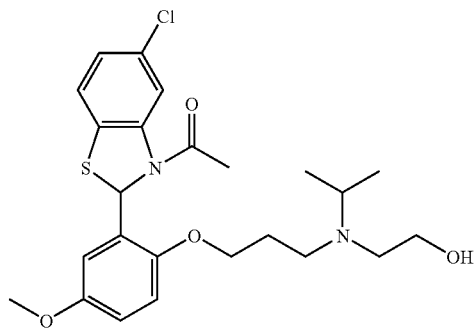

3-Acetyl-6-chloro-2-[2-(3-(N-(2-hydroxyethyl)-N-isopropylamino)-1-methylpropoxy)-5-methoxyphenyl]benzothiazoline

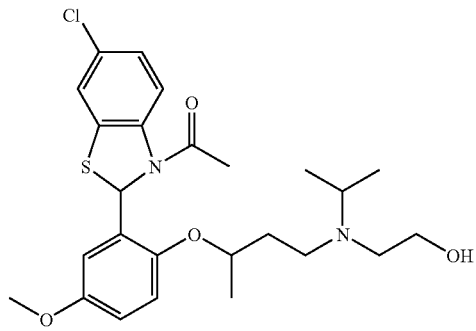

3-Acetyl-2-[2-(3-(2-ethoxyethyl)-N-isopropylamino)propoxy)-5-methoxyphenyl]benzothiazoline

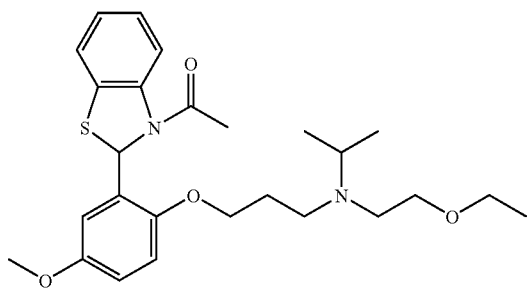

22

(+)-Acetyl-6-chloro-2-[2-(3-(N-isopropyl-N-(2-methoxyethyl)amino)-propoxy)-5-methoxyphenyl]benzothiazoline

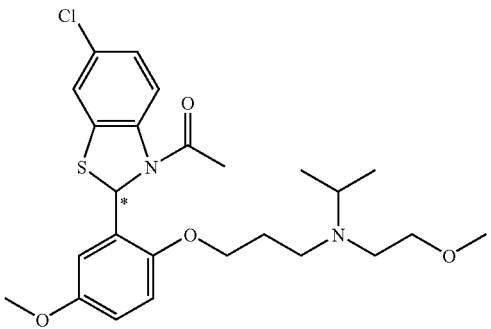

(+)-3-Acetyl-6-chloro-2-[2-(3-(N-(2-hydroxyethyl)-N-isopropylamino)-propoxy)-5-methoxyphenyl]benzothiazoline

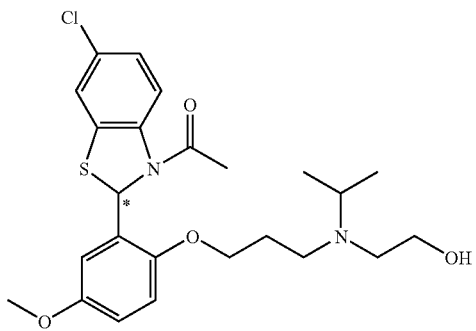

(+)-3-Acetyl-6-chloro-2-[2-(3-(N-(2-ethoxyethyl)-N-isopropylamino)-propoxy)-5-methoxyphenyl]benzothiazoline

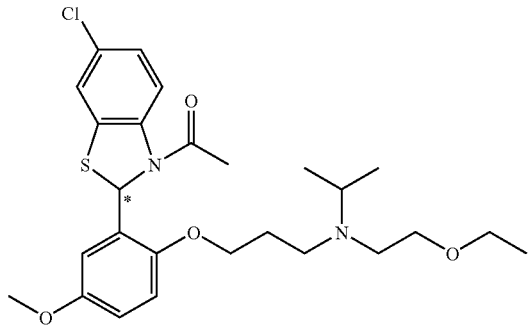

23

(+)-3-Acetyl-2-[2-(3-(N-(2-ethoxyethyl)-N-isopropylamino)propoxy)-5-methoxyphenyl]benzothiazoline

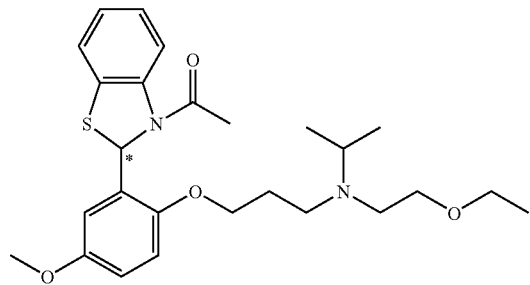

3-Acetyl-6-chloro-2-[2-(3-(N-isopropyl-(N-(2-methoxymethyloxy-ethyl)amino)propoxy)-5-methoxyphenyl]benzothiazoline

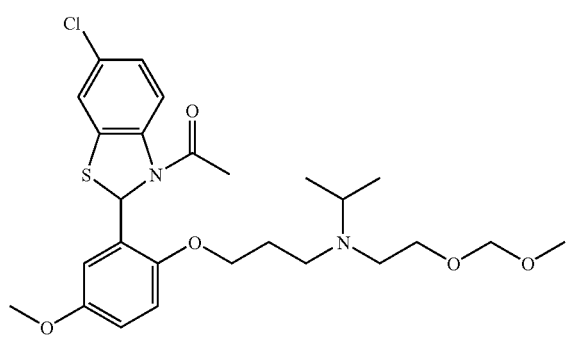

3-Acetyl-6-chloro-2-[2-(3-(N-isopropyl-N-(2-(2-methoxyethoxy-methoxy)ethyl)amino)propoxy)-5-methoxyphenyl]benzothiazoline

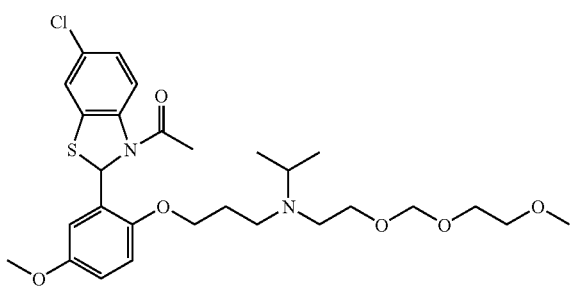

24

2-[2-(3-(N-(2-Acetoxyethyl)-N-isopropylamino)propoxy)-5-methoxyphenyl]-3-acetyl-6-chlorobenzothiazoline

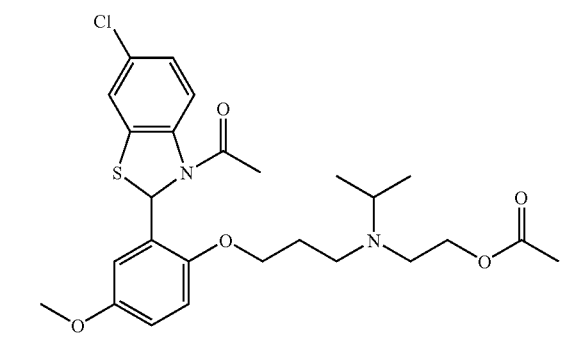

3-Acetyl-6-chloro-2-[2-(3-(N-isopropyl-N-(2-phenylcarboxyethyl)-amino)propoxy)-5-methoxyphenyl]benzothiazoline

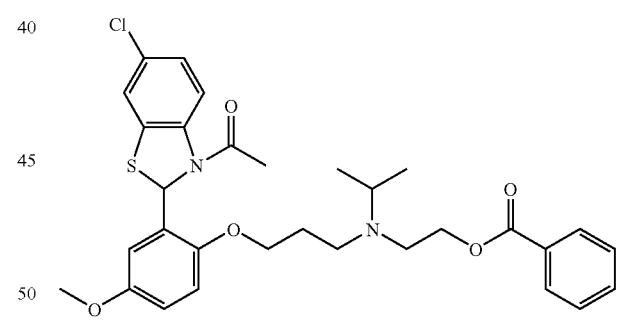

The present compounds can be prepared on the basis of the description of Japanese Laid-open Patent Publication Nos. 46079/1983, 67276/1984, 139679/1985 and 221679/1987. Processes for preparing novel compounds of the present invention will be described below. These compounds can be prepared not only through the following processes for preparation but also through widely-used various processes for preparation. Detailed processes for preparing the present compounds will be described in later Examples (section of Preparation of Present Compounds).

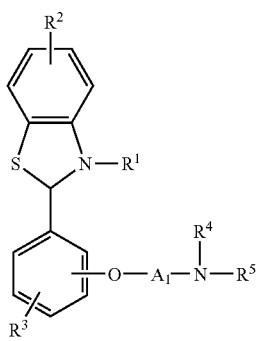

[II]

The present compound [II] can be synthesized according to synthetic route 1. Namely, compound [IV] is reacted with alkyl halide [V] in an organic solvent such as dimethylformamide (DMF) in the presence of a base such as sodium hydride in the range of 0° to 80° C. for 30 minutes to 24 hours to synthesize compound [VI], and then compound [VI] is reacted with amine derivative [VII] in an organic solvent such as DMF in the presence of a base such as potassium carbonate in the range of room temperature to 80° C. for 30 minutes to 24 hours to give the present compound [II].

Synthetic route 1

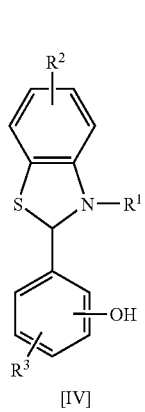

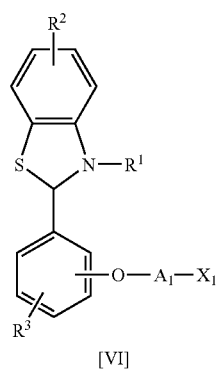

Compound [IV] can be synthesized according to synthetic route 2. Namely, aminothiophenol derivative [VIII] is reacted with aldehyde derivative [IX] in an organic solvent such as toluene at room temperature to 80° C. for 30 minutes to 24 hours, and then a nitrogen of a benzothiazoline ring is acylated with $R^1$ introduction active substance [X] such as N-acetylimizazole to give compound [IV].

Synthetic route 2

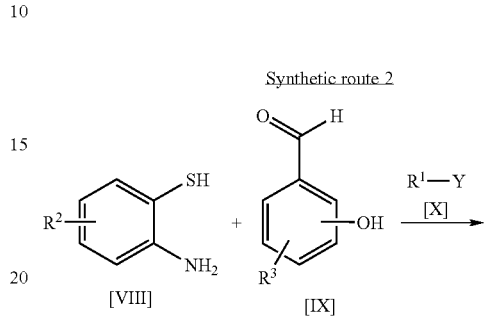

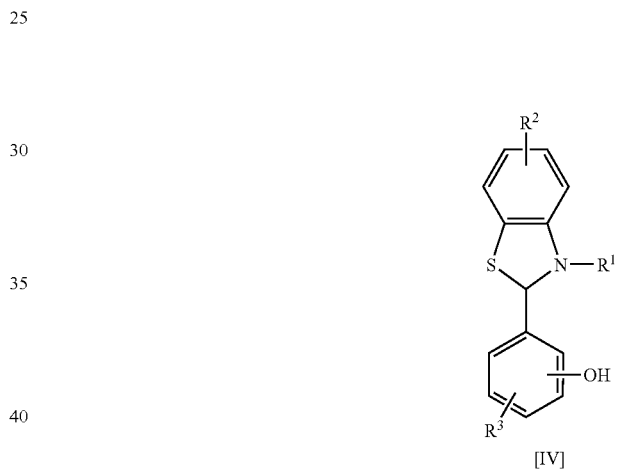

Compound [IV] can be optically resolved according to synthetic route 3 to synthesize respective optically active substances. Namely, compound [IV] is condensed by dehydration with carboxylic acid derivative [XI] in an organic solvent such as DMF in the presence of a catalyst such as dimethylaminopyridine using a condensing agent such as dicyclohexylcarbodiimide to give compound [XII], and then the obtained compound [XII] is fractionally crystallized using a solvent such as ethanol to give optically active substances [XII-A] and [XII-B], which are diastereomers. Further, optically active substances [XII-A] and [XII-B] are hydrolyzed with alkali respectively to give optically active substance [IV-A] exhibiting plus optical rotation and optically active substance [IV-B] exhibiting minus optical rotation. Compounds [VI-A] and [VI-B], which are optical isomers, can be obtained by using these compounds [IV-A] and [IV-B] as the starting materials of the process represented by the synthetic route 1, and compounds represented by the formulae [II-A] and [II-B], which are optically active substances, can be obtained respectively by reacting the compounds [VI-A] and [VI-B] with the amine derivative represented by the formula.

Synthetic route 3

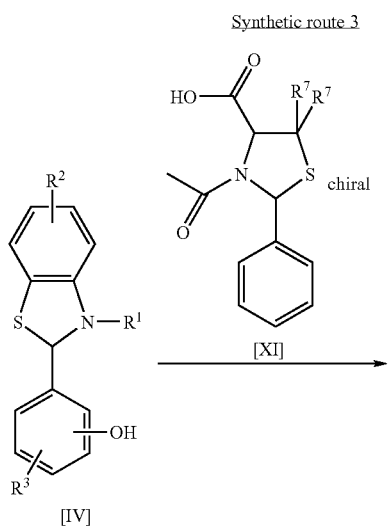

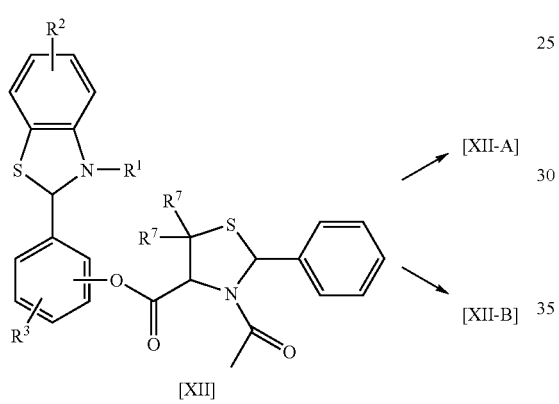

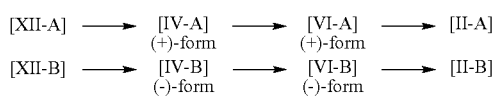

Carboxylic acid derivative [XI] to be used in the above synthetic route can be synthesized by synthetic route 4. Namely, optically active aminothiol derivative [XIII] is reacted with benzaldehyde in a solvent such as water at 0° C. to room temperature for one to 24 hours, and then the resulting crystals are treated in a solvent such as water in the presence of acetic anhydride or the like at room temperature to 80° C. for 30 minutes to 12 hours to give carboxylic acid derivative [XI].

Synthetic route 4

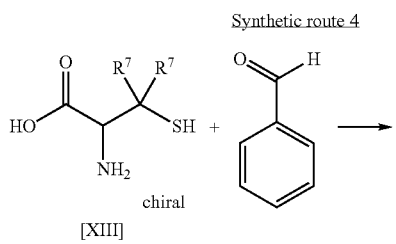

-continued

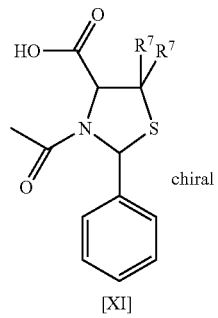

Amine derivative [VII] to be used in the above synthetic route 1 can be synthesized according to the process described in literatures (Japanese Laid-open Patent Publication No. 344821/2000, Tetrahedron 1996, 52, (10), 3473-86, J. Med. Chem. 1973, 16, 736-9 and J. Am. Chem. Soc. 1946, 68, 1582) and synthetic routes 5, 6, 7, 8 and 9.

Namely, in synthetic route 5, compound [XIV] is reacted with alkyl halide [XV] in an organic solvent such as DMF in the presence of a base such as potassium carbonate at room temperature to 80° C. for 30 minutes to 24 hours to give amine derivative [VII].

Synthetic route 5

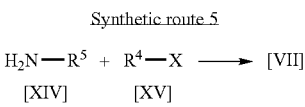

In synthetic route 6, compound [XVI] is reacted with dibutyl dicarbonate in an organic solvent such as tetrahydrofuran at 0° C. to room temperature for 30 minutes to 24 hours, the resulting compound [XVII] is reacted with alkyl halide in an organic solvent such as DMF in the presence of a base such as sodium hydride at 0° C. to room temperature for 30 minutes to 24 hours, and then the resulting compound [XVIII] is deprotected with reagent such as a solution of hydrogen chloride in ethyl acetate to give amine derivative [VII].

Synthetic route 6

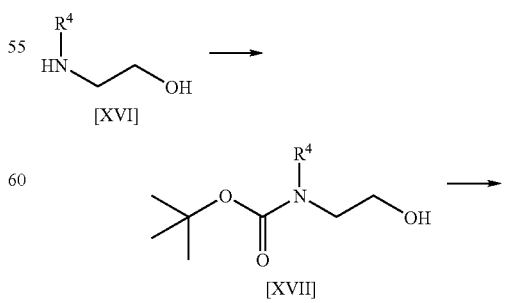

-continued

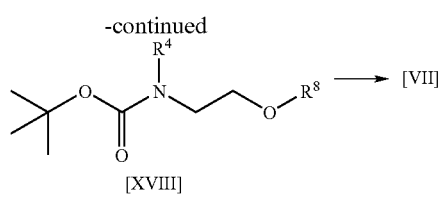

[XVIII]

In synthetic route 7, compound [XIX] is reacted with compound [XX] in an organic solvnt such as DMF in the presence of a base such as potassium carbonate at room temperature to 80° C. for 30 minutes to 24 hours to give amine derivative [VII].

Synthetic route 7

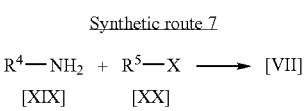

In synthetic route 8, amine derivative [XIX] is reacted with aldehyde derivative [XXI] in an organic solvent such as benzene in the presence of anhydrous sodium sulfate at room temperature to 60° C. for one to 24 hours, and the reaction product is reduced with a reducing agent such as sodium borohydride to give amine derivative [VII].

Synthetic route 8

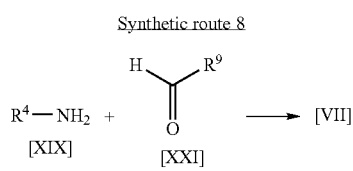

In synthetic route 9, amine derivative [XIX] is reacted with carbonyl compound [XXII] in an organic solvent such as methylene chloride in the presence of a base such as N-methylmorpholine at 0° C. to room temperature for 30 minutes to 24 hours, and then the resulting amide compound [XXIII] is reacted with a reducing agent such as lithium aluminum hydride in an organic solvent such as diethyl ether at 0° to 40° C. for 30 minutes to 24 hours to give amine derivative [VII].

Synthetic route 9

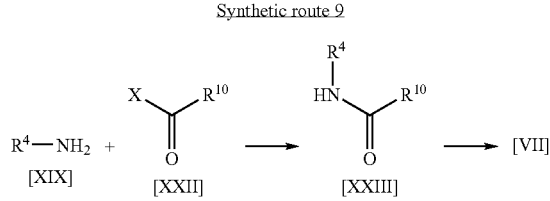

The present compound [II] can be synthesized according to synthetic route 10 other than synthetic route 2. Namely, compound [IV] is reacted with alcohol derivative [XXIV] in an organic solvent such as tetrahydrofuran in the presence of a condensing agent such as triphenylphosphine and diisopropyl azodicarboxylate at 0° to 40° C. for 30 minutes to 24 hours to give the compound [II].

Synthetic route 10

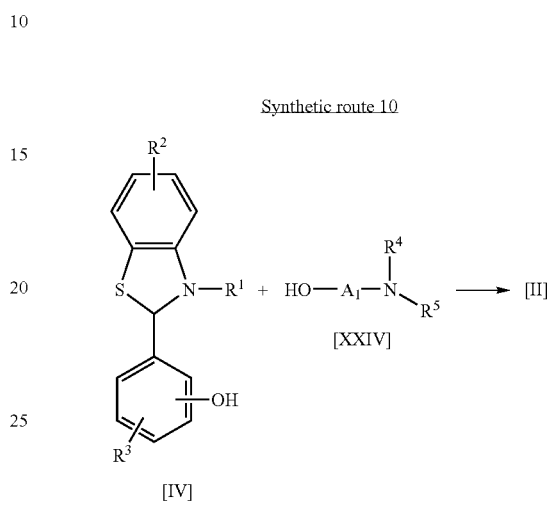

The present compound [II] can be synthesized according to synthetic route 11 other than synthetic route 2. Namely, compound [XXV] (compound included in compound [III] synthesized in synthetic route 1) is reacted with acyl halide [XXVI] or alkyl halide [XXVII] in an organic solvent such as methylene chloride in the presence of a base such as pyridine at 0° to 40° C. for 30 minutes to 24 hours to give the compound [II].

Synthetic route 11

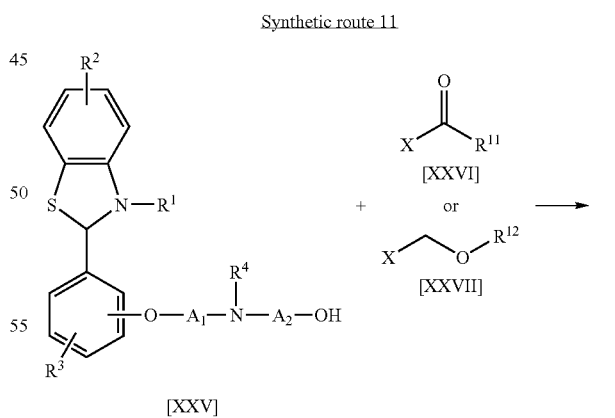

The present compound [II] can be synthesized according to synthetic route 12 other than synthetic route 2. Namely, compound [XXVIII] (compound included in compound [III] synthesized in synthetic route 1) is reacted with alkyl halide [XXIX] in an organic solvent such as DMF in the presence of potassium carbonate at room temperature to 80° C. for 30 minutes to 24 hours to give the compound [II].

Synthetic route 12

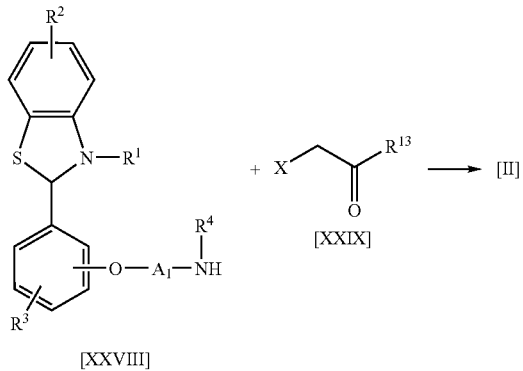

[XXVIII]

The present compounds prepared by the above synthetic routes can be converted into the above-mentioned salts using widely-used techniques.

In order to find new pharmacological actions of the present compounds, agonist activity tests of the present compounds on a κ opioid receptor in a GTP binding activity measurement system were carried out, and effects of the present compounds in the tests were evaluated. Details will be described in later Example (section of pharmacological tests). The present compounds were found to have excellent κ opioid receptor agonist activities (actions). Further, antinociceptive action tests by a mouse acetic acid writhing method were carried out in order to confirm that the present compounds having the κ opioid receptor agonist actions have analgesic effects. As a result, the present compounds were found to have excellent analgesic effects.

As mentioned above, it was reported that the agonist action on the κ opioid receptor is closely related to the analgesic actions and antipruritic actions, and the present compounds are expected to serve as drugs which can control pain and pruritus due to various diseases such as rheumatic diseases such as rheumatoid arthritis, systemic lupus erythematodus, osteoarthritis, gout and rheumatic fever.

The present compounds can be administered orally or parenterally. Examples of dosage forms are a tablet, a capsule, granule, powder, an injection, an ophthalmic solution. The preparations can be prepared by the usual methods.

For example, oral preparations such as a tablet, a capsule, granule and powder can be prepared by optionally adding an excipient such as lactose, mannitol, starch, crystalline cellulose, light silicic acid anhydride, calcium carbonate or calcium hydrogenphosphate, a lubricant such as stearic acid, magnesium stearate or talc, a binder such as starch, hydroxypropylcellulose, hydroxypropylmethylcellulose or polyvinylpyrrolidone, a disintegrator such as carboxymethylcellulose, low substituted hydroxypropylcellulose or calcium citrate, a coating agent such as hydroxypropylmethylcallulose, macrogol or a silicone resin, a stabilizer such as ethyl p-hydroxybenzoate or benzyl alcohol, or a corrigent such as a sweetening agent, a sour agent or a perfume.

Parenteral preparations such as an injection and an ophthalmic solution can be prepared by optionally adding an isotonic agent such as sodium chloride or concentrated glycerin, a buffer such as sodium phosphate or sodium acetate, a surfactant such as polyoxyethylene sorbitan monooleate, polyoxy 40 stearate or polyoxyethylene hydrogenated castor oil, a stabilizer such as sodium citrate or disodium edetate or a preservative such as benzalkonium chloride or paraben.

The dosage of the present compound can be appropriately selected depending on symptoms, age, dosage form or the like. For example, in the case of oral preparations, the usually daily dosage is 0.1 to 5,000 mg, preferably 1 to 1,000 mg, which can be given in a single dose or several divided doses.

BEST MODE FOR CARRYING OUT THE INVENTION

Examples of preparations and formulations of the present compounds and results of pharmacological tests are shown below. These examples do not limit the scope of the present invention, but are intended to make the present invention more clearly understandable.

REFERENCE EXAMPLE 1

3-Acetyl-6-chloro-2-(2-hydroxy-5-methoxyphenyl) benzothiazoline (Reference compound No. 1-1)

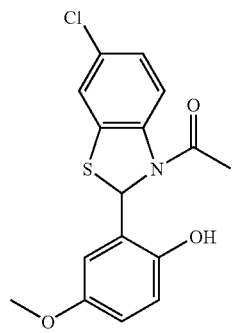

A solution of 2-hydroxy-5-methoxybenzaldehyde (65.0 g, 427 mmol) in toluene (59 ml) and methanol (7 ml) was added to a solution of 2-amino-5-chlorothiophenol (67.7 g, 427 mmol) in toluene (117 ml) and methanol (13 ml) under a nitrogen stream at room temperature, and the mixture was stirred at 50° to 70° C. for 40 minutes. The temperature was returned to room temperature, and then N-acetylimidazole (100 g, 908 mmol) and toluene (65 ml) were added thereto successively. The whole was stirred at room temperature overnight, then chloroform (2,000 ml) and 1 N hydrochloric acid (650 ml×2) were added to the reaction mixture, and the whole was extracted. The organic layer was washed with a saturated aqueous sodium hydrogencarbonate solution (650 ml×2) and saturated-brine (650 ml) successively, dehydrated with anhydrous magnesium sulfate and filtered, and the filtrate was concentrated under reduced pressure. The residue was suspended in chloroform (650 ml), and the suspension was allowed to stand at room temperature overnight. The precipitated crystals were filtered off to give 76.1 g (53%) of the target compound.

IR (KBr) 3296, 3072, 1636, 1502, 1456, 1444, 1374, 1320, 1272, 1195, 1037, 799 $cm^{-1}$

REFERENCE EXAMPLE 2

3-Acetyl-2-(2-hydroxy-5-methoxyphenyl)-5-trifluoromethyl-benzothiazoline (Reference compound No. 2-1)

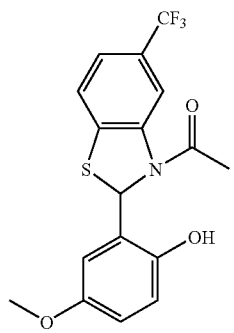

The target compound (2.2 g, 47%) was obtained from 2-amino-4-trifluoromethylthiophenol (3.3 g) by a method similar to Reference Example 1.
IR (KBr) 3362, 1660, 1506, 1429, 1332 cm$^{-1}$

REFERENCE EXAMPLE 3

3-Acetyl-2-(2-hydroxy-5-methoxyphenyl)benzothiazoline (Reference compound No. 3-1)

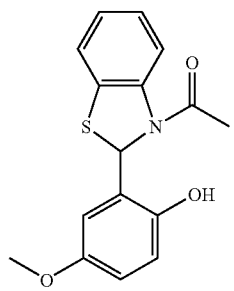

The target compound (92.9 g, 77%) was obtained from 2-aminothiophenol (50.0 g) by a method similar to Reference Example 1.

REFERENCE EXAMPLE 4

3-Acetyl-5-chloro-2-(2-hydroxy-5-methoxyphenyl)benzothiazoline (Reference compound No. 4-1)

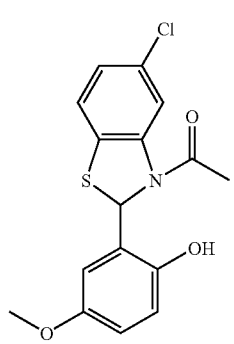

A solution of 2-hydroxy-5-methoxybenzaldehyde (10.0 g, 65.7 mmol) in methanol (20 ml) was added to a solution of 2-amino-4-chlorothiophenol (10.5 g, 65.7 mmol) in methanol (20 ml) under a nitrogen stream at room temperature, the mixture was stirred at room temperature for 50 minutes, and then the precipitated crystals were filtered off. Acetic anhydride (20 ml, 212 mmol) was added to the obtained crystals, the mixture was stirred at room temperature overnight, and then the reaction mixture was concentrated under reduced pressure. Methanol (60 ml), water (10 ml) and potassium carbonate (5.0 g) were added to the residue, the whole was stirred at room temperature overnight, and then the reaction mixture was concentrated under reduced pressure. Ethyl acetate (300 ml) and 1 N-hydrochloric acid (200 ml) were added to the residue, and the whole was extracted. The organic layer was washed with saturated brine (150 ml), dehydrated with anhydrous magnesium sulfate and filtered, and the filtrate was concentrated under reduced pressure. The residue was purified by silica gel column chromatography (mobile phase: hexane/ethyl acetate=3/1) to give 7.7 g (60%) of the target compound.
IR (neat) 3307, 2953, 1650, 1505, 1464, 1434, 1409, 1383, 1284, 1042, 809, 756 cm$^{-1}$

REFERENCE EXAMPLE 5

(+)-3-Acetyl-6-chloro-2-(2-hydroxy-5-methoxyphenyl)benzothiazoline (Reference compound No. 5-1)

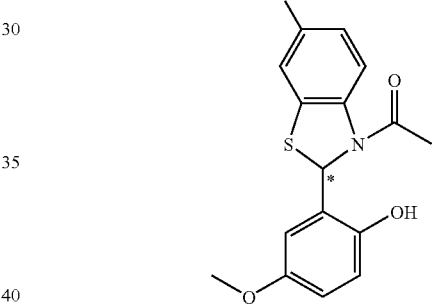

(a) (2R, 4R)-3-Acetyl-2-phenyl-4-thiazolidinecarboxylic acid (Reference compound No. 5-1a)

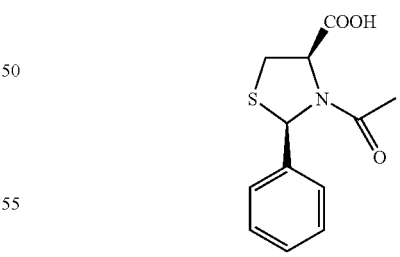

A solution of sodium hydroxide (91.2 g, 2.28 mol) in water (1,500 ml) and a solution of benzaldehyde (232 ml) in methanol (1,500 ml) were added successively to a solution of L-cysteine (400 g, 2.28 mol) in water (1,500 ml) at room temperature, and the mixture was stirred for 15 minutes. The mixture was allowed to stand at room temperature overnight, and then the precipitated crystals were filtered off and dried. Acetic anhydride (1,000 ml, 11.4 mol) was added dropwise to a solution of the obtained crystals in water (1,200 ml) at 60° C.

over 25 minutes. The mixture was stirred at the temperature for 15 minutes, and then the reaction mixture was allowed to stand under ice-cooling overnight. The precipitated crystals were filtered off and dried to give 261.2 g (46%) of the target compound.

IR (KBr) 1717, 1603, 1419, 1281, 1236, 1214 cm$^{-1}$ (b) (2S,4S)-3-Acetyl-5,5-dimethyl-2-phenyl-4-thiazolidinecarboxylic acid (Reference compound No. 5-1b)

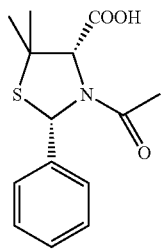

A solution of benzaldehyde (102 ml, 1.01 mol) in ethanol (300 ml) was added to a solution of D-penicillamine (150 g, 1.01 mol) in water (900 ml) at room temperature. The mixture was stirred at room temperature for 15 minutes and under ice-cooling for 1.5 hours, and then the precipitated crystals were filtered off and dried. Acetic anhydride (480 ml, 5.05 mol) was added dropwise to a solution of the obtained crystals in water (700 ml) at 60° C. over 15 minutes. The mixture was stirred at the temperature for 15 minutes, then at room temperature for 15 minutes and under ice-cooling for 1.5 hours, and the precipitated crystals were filtered off and dried to give 252.3 g (89%) of the target compound.

IR (neat) 3392, 2920, 1730% 1618, 1411, 1196, 1178, 732 cm$^{-1}$ (c) (+)-3-Acetyl-2-[2-((2R,4R)-3-acetyl-2-phenylthiazolidin-4-ylcarbonyloxy)-5-methoxyphenyl]-6-chlorobenzothiazoline (Reference compound No. 5-1c)

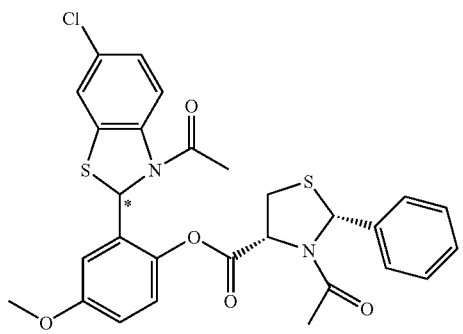

(2R,4R)-3-Acetyl-2-phenyl-4-thiazolidinecarboxylic acid (5.87 g, 2.34 mmol) and N,N-dimethylaminopyridine (290 mg, 2.34 mol) were added to a solution of 3-acetyl-6-chloro-2-(2-hydroxy-5-methoxyphenyl)benzothiazoline (5.24 g, 1.56 mmol) in anhydrous DMF (60 ml) at room temperature. After ice-cooling, dicyclohexylcarbodiimide (3.54 g, 1.71 mmol) was added thereto, and the mixture was stirred under ice-cooling for one hour and at room temperature for two hours. After ice-cooling, water (1 ml) was added to the reaction mixture, the whole was stirred at room temperature and then concentrated under reduced pressure, and chloroform (30 ml) was added to the residue. The resulting insoluble matter was filtered out, water (120 ml) was added to the mother liquor, and the whole was extracted with chloroform (50 ml). The organic layer was washed with a 10% aqueous citric acid solution (120 ml), a saturated aqueous sodium hydrogencarbonate solution (120 ml) and saturated brine (100 ml) successively, and dehydrated with anhydrous magnesium sulfate. Chloroform was evaporated under reduced pressure, chloroform (15 ml) was added to the residue, the resulting insoluble matter was filtered out, and the mother liquor was concentrated under reduced pressure. Ethanol (600 ml) was added to the residue, the residue was dissolved by heating, and then the solution was allowed to stand at room temperature overnight. The precipitated crystals were filtered off and dried to give 3.87 g (43%) of the target compound.

IR (KBr) 3425, 1765, 1673, 1654, 1576, 1492, 1463 1142 cm$^{-1}$ (d-1) (+)-3-Acetyl-2-[2-((2S,4S)-3-acetyl-5,5-dimethyl-2-phenylthiazolidin-4-ylcarbonyloxy)-5-methoxyphenyl]-6-chlorobenzothiazoline (Reference compound No. 5-1d-1)

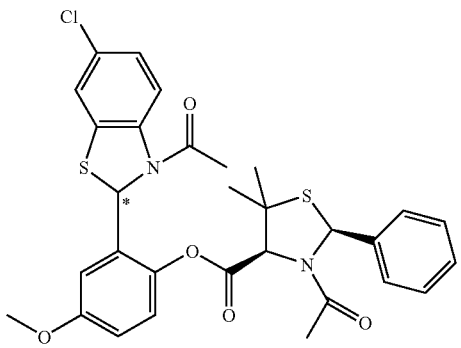

A solution of (2S,4S)-3-acetyl-5,5-dimethyl-2-phenyl-4-thiazolidinecarboxylic acid (102 g, 0.38 mol) in anhydrous DMF (500 ml) was added to a solution of 3-acetyl-6-chloro-2-(2-hydroxy-5-methoxyphenyl)benzothiazoline (127 g, 0.38 mol) in anhydrous DMF (500 ml) at room temperature. N,N-Dimethylaminopyridine (5.58 g, 45.7 mmol) was added thereto under a nitrogen atmosphere at room temperature with stirring. After ice-cooling, diethyl azodicarboxylate (87 g, 0.50 mol) was added thereto, and then the mixture was stirred under ice-cooling for 15 minutes, at room temperature for one hour and further at an internal temperature of about 40° C. for three days. The reaction mixture was concentrated under reduced pressure, a 10% aqueous citric acid solution (1,000 ml) was added to the residue, and the whole was extracted with ethyl acetate (1,000 ml). The organic layer was washed with water (1,000 ml) and saturated brine (1,000 ml) successively and dehydrated with magnesium sulfate. Ethyl acetate was evaporated under reduced pressure, a mixed solvent (ethanol/diisopropyl ether=200 ml/1,000 ml) was added to the residue, the residue was dissolved by heating, and then the solution was allowed to stand at room temperature overnight. One precipitated diastereomer was filtered out, and the mother liquor was concentrated under reduced pressure. The residue was purified by silica gel column chromatography (mobile phase:hexane/ethyl acetate=1/1) to give 78.0 g (43%) of the target compound.

IR (neat) 3009, 1679, 1650, 1495, 1464, 1380, 1322, 1176, 1140, 757 cm⁻

(d-2) (+)-3-Acetyl-2-[2-((2S,4S)-3-acetyl-5,5-dimethyl-2-phenylthiazolidin-4-ylcarbonyloxy)-5-methoxyphenyl]-6-chlorobenzothiazoline (Reference compound No. 5-1d)

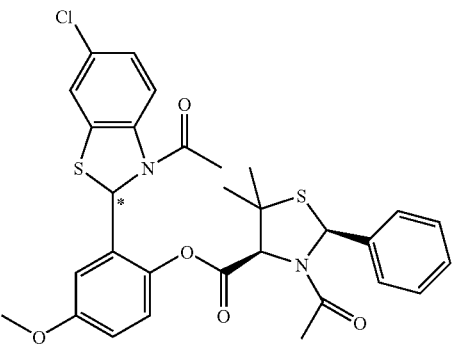

(2S,4S)-3-Acetyl-5,5-dimethyl-2-phenyl-4-thiazolidine-carboxylic acid (6.2 g, 22.2 mmol) was added to a solution of 3-acetyl-6-chloro-2-(2-hydroxy-5-methoxyphenyl)benzothiazoline (5 g, 14.9 mmol) in anhydrous DMF (20 ml) at room temperature. N,N-Dimethylaminopyrdine (270 mg, 2.21 mmol) was added thereto under a nitrogen atmosphere at room temperature with stirring. After ice-cooling, dicyclohexylcarbodiimide (3.1 g, 15.0 mmol) was added thereto, the mixture was stirred under ice-cooling for 15 minutes and at room temperature for three days, then ethyl acetate (100 ml) and water (100 ml) were added to the reaction mixture, and the whole was stirred at room temperature. The precipitated insoluble matter was filtered out, and the mother liquor was washed with a 10% citric acid solution (100 ml), water (100 ml) and saturated brine (100 ml) successively and dehydrated with anhydrous magnesium sulfate. Ethyl aceate was evaporated under reduced pressure, ethanol (50 ml) was added to the residue, the residue was dissolved by heating, and then the solution was allowed to stand at room temperature overnight. One precipitated diastereomer was filtered out, the mother liquor was concentrated under reduced pressure, and the residue was purified by silica gel column chromatography (mobile phase:hexane/ethyl acetate 1/1) to give 4.2 g (47%) of the target compound.

(e) (+)-3-Acetyl-6-chloro-2-(2-hydroxy-5-methoxyphenyl)-benzothiazoline (Reference compound No. 5-1)

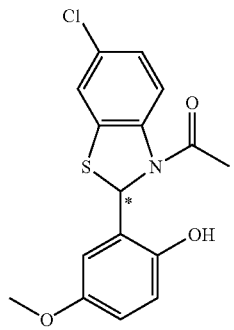

A 1 N aqueous sodium hydroxide solution (970 ml) was added dropwise to a solution of (+)-3-acetyl-2-[2-((2S,4S)-3-acetyl-5,5-dimethy-2-phenylthiazolidin-4-ylcarbonyloxy)-5-methoxyphenyl]-6-chlorobanzothiazoline (193 g, 0.32 mol) in DMF (2,000 ml) under ice-cooling, and the mixture was stirred for 30 minutes. 1 N Hydrochloric acid was added to the reaction mixture at the temperature to acidify it, and the whole was extracted with ethyl acetate (4,000 ml). The organic layer was washed with saturated brine (4,000 ml) and dehydrated with anhydrous magnesium sulfate. Ethyl acetate was evaporated under reduced pressure, chloroform (400 ml) was added to the residue, and the precipitated crystals were filtered off and dried to give 55.9 g of the target compound. The mother liquor was concentrated under reduced pressure, and the same operation was repeated to give 79.5 g (74%) of the target compound finally.

IR (neat) 3068, 1644, 1466, 1384, 1277, 1257, 1196, 1091, 808 cm⁻¹

REFERENCE EXAMPLE 6

(+)-3-Acetyl-2-(2-hydroxy-5-methoxyphenyl)benzothiazoline (Reference compound No. 6-1)

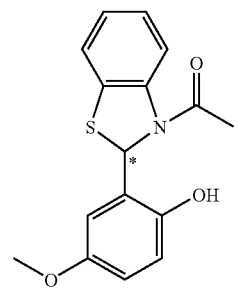

(a) (+)-3-Acetyl-2-[2-((2R,4R)-3-acetyl-2-phenylthiazolidin-4-ylcarbonyloxy)-5-methoxyphenyl]benzothiazoline (Reference compound No. 6-1a)

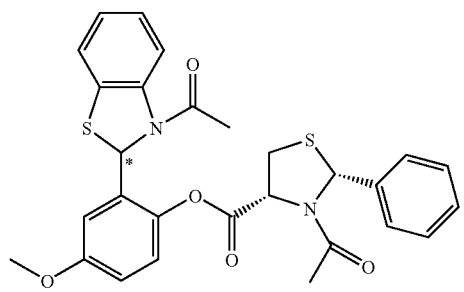

The target compound (20.0 g, 83%) was obtained from 3-acetyl-2-(2-hydroxy-5-methoxyphenyl)benzothiazoline (27.4 g) by a method similar to Reference Example 5 (c).

IR (KBr) 3039, 2933, 1765, 1674, 1657, 1587, 1491, 1465 cm⁻¹

(b) (+)-3-Acetyl-2-(2-hydroxy-5-methoxyphenyl) benzothiazoline (Reference compound No. 6-1)

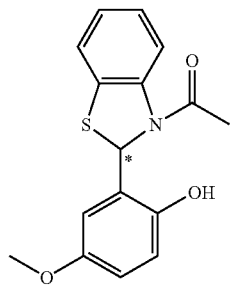

The target compound (10.6 g, 95%) was obtained from (+)-3-acetyl-2-[2-((2R,4R)-3-acetyl-2-phenylthiazolidin-4-ylcarbonyloxy)-5-methoxyphenyl]benzothiazoline (19.9 g) by a method similar to Reference Example 5 (e).

REFERENCE EXAMPLE 7

(−)-3-Acetyl-6-chloro-2-(2-hydroxy-5-methoxyphenyl)benzothiazoline (Reference compound No. 7-1)

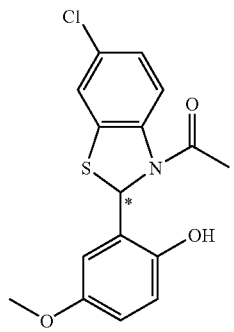

(a) (−)-3-Acetyl-2-[2-((2S,4S)-3-acetyl-5,5-dimethyl-2-phenylthiazolidin-4-ylcarbonyloxy)-5-methoxyphenyl]-6-chlorobenzothiazoline (Reference compound No. 7-1a)

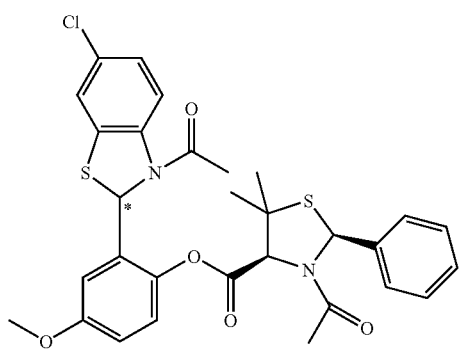

A solution of (2S,4S)-3-acetyl-5,5-dimethyl-2-phenyl-4-thiazolidinecarboxylic acid [compound described in Reference Example 4 (b)] (102 g, 0.38 mol) in anhydrous DMF (500 ml) was added to a solution of 3-acetyl-6-chloro-2-(2-hydroxy-5-methoxyphenyl)-benzothiazoline (127 g, 0.38 mol) in anhydrous DMF (500 ml) at room temperature. N,N-Dimethylaminopyridine (5.58 g, 45.7 mmol) was added thereto under a nitrogen-atmosphere at room temperature with stirring. After ice-cooling, diethyl azodicarboxylate (87 g, 0.50 mol) was added thereto. The mixture was stirred under ice-cooling for 15 minutes, at room temperature for one hour and further at an internal temperature of about 40° C. for three days. The reaction mixture was concentrated under reduced pressure, a 10% aqueous citric acid solution (1,000 ml) was added to the residue, and the whole was extracted with ethyl acetate (1,000 ml). The organic layer was washed with water (1,000 ml) and saturated brine (1,000 ml) successively and dehydrated with magnesium sulfate, and ethyl acetate was evaporated under reduced pressure. A mixed solvent (ethanol/diisopropyl ether=200 ml/1000 ml) was added to the residue, the residue was dissolved by heating, and then the solution was allowed to stand at room temperature overnight. The precipitated crystals were filtered off and dried to give 34.7 g of the target compound. The mother liquor was concentrated under reduced pressure, and the residue was purified by silica gel column chromatography (mobile phase:hexane/ethyl acetate=1/1) to give further 43.8 g of the target compound (total 43%).

IR (neat) 3008, 1680, 1654, 1494, 1464, 1383, 1139, 755 cm$^{-1}$ (b) (−)-3-Acetyl-6-chloro-2-hydroxy-5-methoxyphenyl)-benzothiazoline (Reference compound No. 7-1)

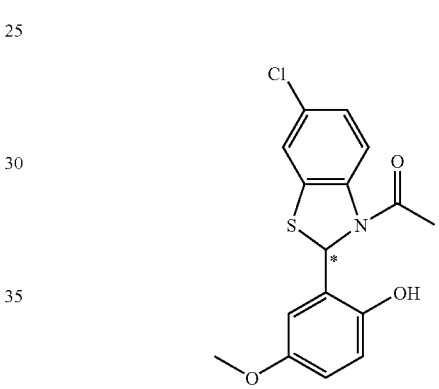

The target compound (33.7 g, 77%) was obtained from (−)-3-acetyl-2-[2-((2S,4S)-3-acetyl-5,5-dimethyl-2-phenylthiazolidin-4-ylcarbonyloxy)-5-methoxyphenyl]-6-chlorobenzothiazolidine (78.3 g) by a method similar to Reference Example 4 (e).

IR (KBr) 3068, 1643, 1509, 1467, 1385, 1350, 1277, 1196, 1092, 808 cm$^{-1}$

REFERENCE EXAMPLE 8

3-Acetyl-2-[2-(3-bromopropoxy)-5-methoxyphenyl]benzothiazoline (Reference compound No. 8-1)

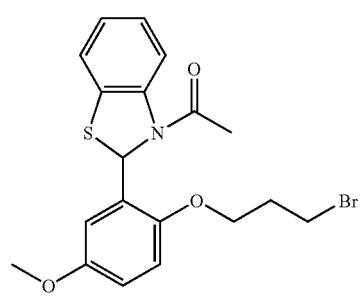

Potassium carbonate (27.5 g, 19.9 mmol) and 1,3-dibromopropane (105 ml, 1.03 mol) were added to a solution of 3-acetyl-2-(2-hydroxy-5-methoxyphenyl)benzothiazoline (30.0 g, 8.93 mmol) in 2-propanol (200 ml). The mixture was refluxed for two hours and cooled to room temperature, then water (300 ml) was added to the reaction mixture, and the whole was extracted with ethyl acetate (500 ml) twice. The ethyl acetate layer was washed with saturated brine (100 ml) twice, dehydrated with anhydrous magnesium sulfate, filtered and concentrated. The residue was purified by silica gel column chromatography (mobile phase:hexane/ethyl acetate=2/1). Diisopropyl ether was added to the obtained oily matter, and the mixture was refluxed to dissolve the oily matter. The solution was allowed to stand, and then the precipitated crystals were filtered off to give 32.1 g (76%) of the target compound.

IR (KBr) 2952, 1672, 1591, 1576, 1499, 1468, 1379, 1278, 1210 cm$^{-1}$

REFERENCE EXAMPLE 9

3-Acetyl-6-chloro-2-[2-(3-chloropropoxy)-5-methoxyphenyl]-benzothiazoline (Reference compound No. 9-1)

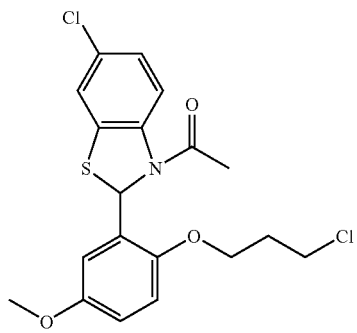

A solution of 3-acetyl-6-chloro-2-(2-hydroxy-5-methoxyphenyl)-benzothiazoline (4.68 g, 14.4 mol) in DMF (15 ml) and 1-bromo-3-chloropropane (4.2 ml, 167 mmol) were added to a solution of 60% sodium hydride (680 mg, 17.0 mmol) in DMF (15 ml) successively under a nitrogen atmosphere under ice-cooling. The mixture was stirred at 50° C. for one hour, and then the reaction mixture was allowed to stand to room temperature. A saturated aqueous ammonium chloride solution (5 ml) and water (50 ml) were added to the reaction mixture, and the whole was extracted with ethyl acetate (50 ml) twice. The ethyl acetate layer was washed with saturated brine (30 ml) twice, dehydrated with anhydrous magnesium sulfate, filtered and concentrated under reduced pressure. Methanol was added to the obtained oily matter, and the oily matter was dissolved by heating. The solution was allowed to stand, and then the precipitated crystals were filtered off to give 5.39 g (94%) of the target compound.

IR (KBr) 2912, 1676, 1458, 1373, 1281, 1206, 1026 cm$^{-1}$

REFERENCE EXAMPLE 10

3-Acetyl-6-chloro-2-[2-(2-bromoethoxy)-5-methoxyphenyl]-benzothiazoline (Reference compound No. 10-1)

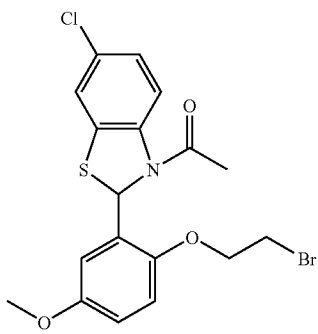

The target compound (2.2 g, 67%) was obtained from 3-acetyl-6-chloro-2-(2-hydroxy-5-methoxyphenyl)benzothiazoline (2.5 g) by a method similar to Reference Example 7.

IR (KBr) 1666, 1574, 1498, 1464, 1377, 1216 cm$^{-1}$

REFERENCE EXAMPLE 11

3-Acetyl-5-chloro-2-[2-(3-chloropropoxy)-5-methoxyphenyl]-benzothiazoline (Reference compound No. 11-1)

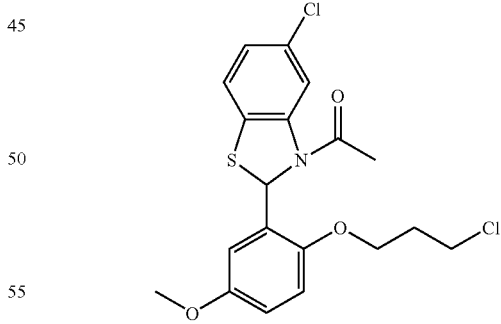

The target compound (3.3 g, 78%) was obtained from 3-acetyl-5-chloro-2-(2-hydroxy-5-methoxyphenyl)benzothiazoline (3.5 g) by a method similar to Reference Example 7.

IR (KBr) 2930, 1677, 1463, 1380, 1281, 1211, 1031, 806 cm$^{-1}$

REFERENCE EXAMPLE 12

3-Acetyl-2-[2-(3-chloropropoxy)-5-methoxyphenyl]-5-trifluoromethylbenzothiazoline (Reference compound No. 12-1)

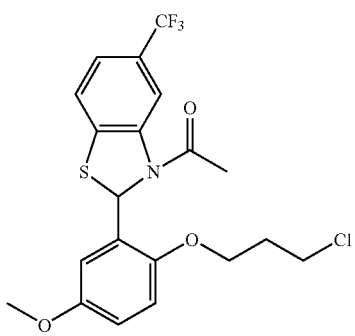

The target compound (1.9 g, 89%) was obtained from 3-acetyl-2-(2-hydroxy-5-methoxyphenyl)-5-trifluoromethyl-benzothiazoline (1.8 g) by a method similar to Reference Example 7.

IR (KBr) 2962, 1680, 1600, 1500, 1431, 1388, 1323 $cm^{-1}$

REFERENCE EXAMPLE 13

3-Acetyl-6-chloro-2-[2-(1-methyl-3-p-toluenesulfonyloxypropoxy)-5-methoxyphenyl]benzothiazoline (Reference compound No. 13-1)

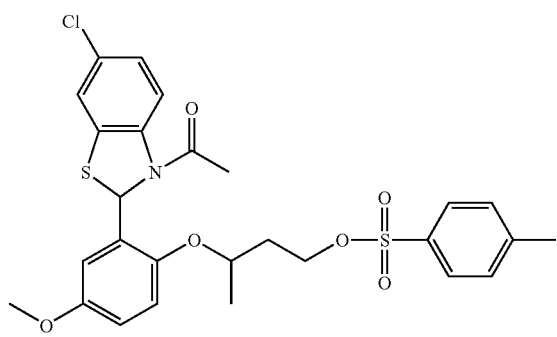

(a) 3-p-Toluenesulfonyloxy-1-methyl-1-propanol (Reference compound No. 13-1a)

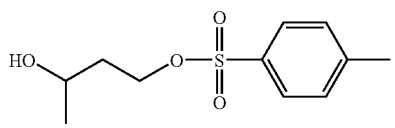

Pyridine (9.0 ml, 111 mmol) was added to a solution of 1,3-butanediol (5.07 g, 56.3 mmol) in anhydrous methylene chloride (20 ml) at room temperature. After ice-cooling, p-toluenesulfonyl chloride (15.9 g, 83.4 mmol) was added thereto, the mixture was stirred at room temperature overnight, then water (60 ml) was added to the reaction mixture, and the whole was extracted with ethyl acetate (100 ml). The ethyl acetate layer was washed with 1 N hydrochloric acid (30 ml) and saturated brine (30 ml) successively and dehydrated with anhydrous magnesium sulfate. Ethyl acetate was evaporated under reduced pressure, and the obtained oily matter was purified by silica gel column chromatography (mobile phase:hexane/ethyl acetate=3/1) to give 7.72 g (57%) of the target compound.

IR (neat) 3543, 3413, 2970, 2929, 1598, 1356, 1176, 948 $cm^{-1}$ (b) 3-Acetyl-6-chloro-2-[2-(1-methyl-3-p-toluenesulfonyloxypropoxy)-5-methoxyphenyl]benzothiazoline (Reference compound No. 13-1)

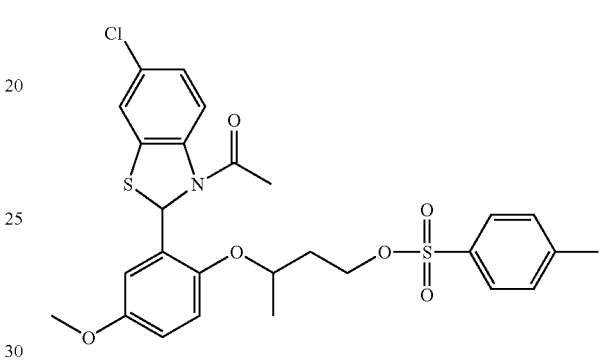

A solution of diisopropyl azodicarboxylate (1.54 g, 7.61 mmol) in anhydrous tetrahydrofuran (10 ml) was added to a solution of 3-acetyl-6-chloro-2-(2-hydroxy-5-methoxyphenyl)benzothiazoline (2.56 g, 7.62 mmol), triphenylphosphine (2.00 g, 7.61 mmol) and 3-p-toluenesulfonyloxy-1-methyl-propanol (1.86 g, 7.61 mmol) in anhydrous tetrahydrofuran (10 ml) at room temperature, and the mixture was stirred for four hours. The reaction mixture was concentrated, and the obtained oily matter was purified by silica gel column chromatography (mobile phase:hexane/ethyl acetate=4/1) to give 1.58 g (37%) of the target compound.

REFERENCE EXAMPLE 14

(+)-3-Acetyl-6-chloro-2-[2-(3-chloropropoxy)-5-methoxyphenyl]-benzothiazoline (Reference compound No. 14-1)

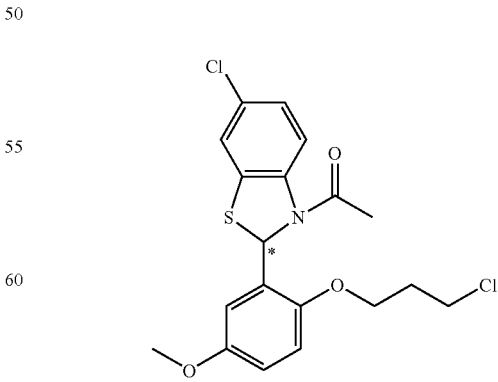

1-Bromo-3-chloropropane (106 ml, 1.07 mol) was added to a solution of 60% sodium hydride (4.50 g, 0.11 mol) in anhydrous DMF (100 ml) under ice-cooling. Next, a solution of (+)-3-acetyl-6-chloro-2-(2-hydroxy-5-methoxyphenyl)benzothiazoline (36.0 g, 0.11 mol) in anhydrous DMF (200 ml) was added dropwise thereto. After dropping, the mixture was further stirred for one hour, then water was added to the reaction mixture, and the whole was extracted with ethyl acetate (1,000 ml). The organic layer was washed with saturated brine (1,000 ml) and dehydrated with anhydrous magnesium sulfate. Ethyl acetate was evaporated under reduced pressure, then methanol (300 ml) was added to the residue, and the mixture was stirred under ice-cooling. The precipitated crystals were filtered off and dried to give 29.0 g (66%) of the target compound.

IR (KBr) 2940, 2835, 1871, 1755, 1671, 1576, 1497, 1464, 1347 cm$^{-1}$

REFERENCE EXAMPLE 15

(−)-3-Acetyl-6-chloro-2-[2-(3-chloropropoxy)-5-methoxyphenyl]-benzothiazoline (Reference compound No. 15-1)

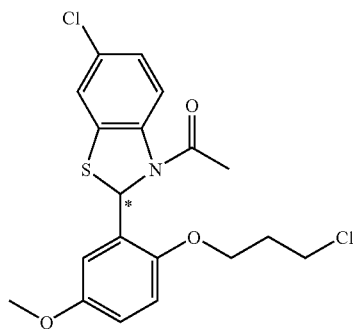

The target compound (44.0 g, quantitatively) was obtained from (−)-3-acetyl-6-chloro-2-(2-hydroxy-5-methoxyphenyl)benzothiazoline (33.7 g) by a method similar to Reference Example 12.

IR (neat) 2961, 2938; 1679, 1498, 1465, 1210, 1048, 810 cm$^{-1}$

REFERENCE EXAMPLE 16

(+)-3-Acetyl-2-[2-(3-chloropropoxy)-5-methoxyphenyl]benzothiazoline (Reference compound No. 16-1)

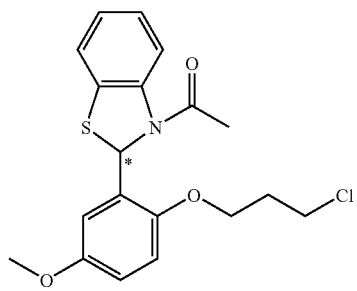

The target compound (3.1 g, 82%) was obtained from (+)-3-aetyl-2-(2-hydroxy-5-methoxyphenyl)benzothiazoline (3.0 g) by a method similar to Reference Example 12.

IR (neat) 2959, 2834, 1675, 1578, 1497, 1466, 1379, 1277, 1210, 1048, 750 cm$^{-1}$

REFERENCE EXAMPLE 17

2-(Cyclohexylmethylamino)ethanol hydrochloride (Reference compound No. 17-1)

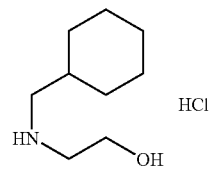

Sodium iodide (11.4 g, 76.2 mmol) was added to a solution of bromomethylcyclohexane (4.50 g, 25.4 mmol) and ethanolamine (7.76 g, 127 mmol) in ethanol (60 ml) at room temperature, and the mixture was refluxed for 18 hours. The temperature was returned to room temperature, and then diethyl ether (60 ml) and a saturated aqueous ammonium chloride solution (80 ml) were added to the reaction mixture. The aqueous layer was basified with a 4 N aqueous sodium hydroxide solution, and the whole was extracted with chloroform (100 ml). The chloroform layer was washed with saturated brine and dehydrated with anhydrous sodium sulfate. Chloroform was evaporated under reduced pressure, and a 4 N solution (10 ml) of hydrogen chloride in dioxane was added to the obtained oily matter at room temperature. The precipitated crystals were filtered off and washed with diethyl ether to give 3.85 g (78%) of the target compound.

IR (KBr) 3317, 3060, 2926, 2851, 1564, 1448, 1430, 1079, 1040 cm$^{-1}$

Similarly 2-(Cyclopropylmethylamino)ethanol hydrochloride (Reference compound No. 17-2)

Yield: 45%

IR (neat) 3358, 2957, 2794, 1592, 1452, 1077, 1029 cm$^{-1}$ 2-(1-Ethylpropylamino)ethanol hydrochloride (Reference compound No. 17-3)

Yield: 60%

IR (neat) 3346, 2971, 1591, 1459, 1075 cm$^{-1}$

REFERENCE EXAMPLE 18

N-Benzyl-2-(methylthio)ethylamine hydrochloride (Reference compound No. 18-1)

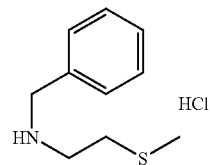

The target compound (1.3 g, 21%) was obtained from 2-(methythio)ethylamine (4.0 g) and benzyl bromide (5.0 g) by a method similar to Reference Example 15.

IR (KBr) 2940, 2792, 2424, 1440, 1439, 746, 702 cm$^{-1}$

REFERENCE EXAMPLE 19

N-(2-Methoxyethyl)cyclopropylmethylamine hydrochloride (Reference compound No. 19-1)

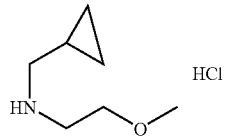

The target compound (1.5 g, 41%) was obtained from 2-methoxyethylamine (3.3 g) and (bromomethyl)cyclopropane (3.0 g) by a method similar to Reference Example 15.

IR (neat) 2949, 2794, 1587, 1453, 1122, 1033 cm$^{-1}$

REFERENCE EXAMPLE 20

N-(2-Ethoxyethyl)isopropylamine (Reference compound No. 20-1)

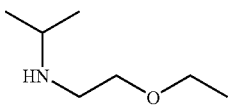

The target compound (70.7 g, 51%) was obtained from 2-ethoxyethylamine (93.8 g) and isopropyl bromide (142 g) by a method similar to Reference Example 15.

IR (neat) 2970, 2933, 2869, 2616, 1469, 1444, 1380 cm$^{-1}$

REFERENCE EXAMPLE 21

N-(2-Benzyloxyethyl)isopropylamine hydrochloride (Reference compound No. 21-1)

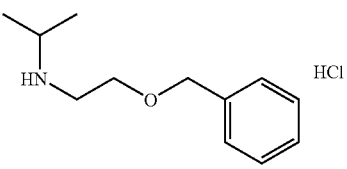

(a) 2-(N-tert-Butoxycarbonyl-N-isopropylamino) ethanol (Reference compound No. 21-1a)

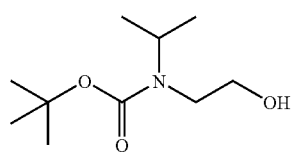

A solution of dibutyl dicarbonate (25.0 g, 116 mmol) in tetrahydrofuran (40 ml) was added to a solution of 2-(isopropylamino)ethanol (10.0 g, 96.9 mmol) in tetrahydrofuran (60 ml) under ice-cooling. The mixture was stirred at room temperature for 3.5 hours, then a 10% aqueous citric acid solution (500 ml) was added to the reaction mixture, and the whole was extracted with ethyl acetate (500 ml). The organic layer was washed with saturated brine (500 ml) and dehydrated with anhydrous magnesium sulfate. Ethyl acetate was evaporated under reduced pressure, and the obtained oily matter was purified by silica gel column chromatography (mobile phase: hexane/ethyl acetate=1/1) to give 24.0 g (quantitatively) of the target compound.

IR (neat) 3438, 1694, 1052 cm$^{-1}$ (b) N-(2-Benzyloxyethyl)-N-(tert-butoxycarbonyl) isopropylamine (Reference compound No. 21-1b)

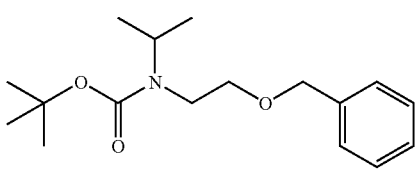

A solution of 2-(N-tert-butoxycarbonyl-N-isopropylamino)-ethanol (3.00 g, 14.8 mmol) and benzyl bromide (2.6 ml, 22.1 mmol) in anhydrous tetrahydrofuran (30 ml) was added to a solution of 60% sodium hydride (885 mg, 22.1 mmol) in anhydrous tetrahydrofuran (20 ml) under ice-cooling, and the mixture was stirred at 60° C. for four hours. Water (100 ml) was added to the reaction mixture under ice-cooling, the temperature was returned to room temperature, and the whole was extracted with ethyl acetate (100 ml). The organic layer was washed with saturated brine (100 ml) and dehydrated with anhydrous magnesium sulfate. Ethyl acetate was evaporated under reduced pressure, and the obtained oily matter was purified by silica gel column chromatography (mobile phase:hexane/ethyl acetate=4/1) to give 1.30 g (30%) of the target compound.

IR (neat) 1693, 1166, 1126, 736, 697 cm$^{-1}$ (c) N-(2-Benzyloxyethyl)isopropylamine hydrochloride (Reference compound No. 21-1)

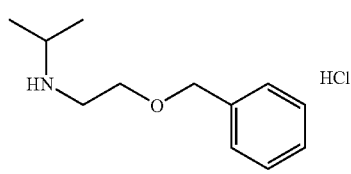

A 4 N solution (3 ml) of hydrogen chloride in ethyl acetate was added to a solution of N-(2-benzyloxyethyl)-N-(tert-butoxycarbonyl)-isopropylamine (1.20 g, 4.09 mmol) in ethyl acetate (3 ml) under ice-cooling. The mixture was stirred at room temperature for five hours, and the reaction mixture was concentrated under reduced pressure. The obtained solid was filtered off with hexane to give 728 mg (77%) of the target compound.

IR (KBr) 2750-2600, 1127, 731, 696 cm$^{-1}$

REFERENCE EXAMPLE 22

N-(2-Methoxybenzyl)isopropylamine hydrochloride (Reference compound No. 22-1)

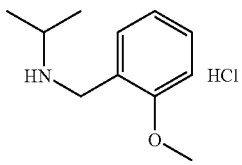

Isopropylamine (2.0 ml, 24 mmol) and anhydrous sodium sulfate (6.00 g, 42 mmol) were added to a solution of 2-methoxybenzaldehyde (3.14 g, 23 mmol) in benzene (6 ml) at room temperature. The mixture was stirred at room temperature overnight, the reaction mixture was filtered, and the filtrate was concentrated under reduced pressure. Methanol (30 ml) was added to the obtained oily matter, and then sodium borohydride (0.87 g, 23 mmol) was added thereto under ice-cooling. The mixture was stirred at room temperature for four hours, saturated brine (15 ml) and water (30 ml) were added to the reaction mixture, and the whole was extracted with ethyl acetate (100 ml). The organic layer was washed with saturated brine (20 ml) and dehydrated with anhydrous magnesium sulfate. Ethyl acetate was evaporated under reduced pressure, ethanol (25 ml) was added to the obtained oily matter, and then 6 N hydrochloric acid (10 ml) was added thereto at room temperature. The reaction mixture was concentrated under reduced pressure, diethyl ether was added to the obtained oily matter, and the resulting crystals were filtered off and washed with ethyl acetate to give 3.00 g (60%) of the target compound.

IR (KBr) 3300-2000, 1606, 1587, 1500, 1465, 1444, 1256 cm$^{-1}$
Similarly

N-(1,3-Thiazol-2-ylmethyl)isopropylamine hydrochloride (Reference compound No. 22-2)

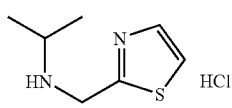

Yield: 89%
IR (KBr) 3352, 2973, 2683, 2554, 2413, 1946, 1693, 1572, 1476, 1388, 1296, 1150, 886, 781 cm$^{-1}$
Similarly

N-(Furan-2-ylmethyl)-N-isopropylamine hydrochloride (Reference compound No. 22-3)

IR (KBr) 2952, 2774, 2573, 2426, 1587, 1447, 1156, 937, 760 cm$^{-1}$
Similarly

N-(Thiophen-2-ylmethyl)-N-isopropylamine hydrochloride (Reference compound No. 22-4)

IR (KBr) 2943, 2727, 2680, 2458, 1594, 1232, 986, 735 cm$^{-1}$

REFERENCE EXAMPLE 23

N-Isopropyl-3-cyclohexyl-1-propylamine hydrochloride (Reference compound No. 23-1)

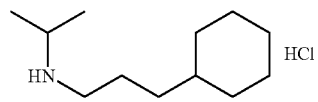

(a) N-Isopropyl-3-cyclohexylpropanamide (Reference compound No. 23-1a)

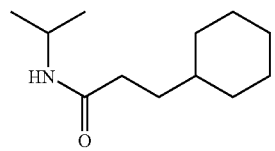

Thionyl chloride (6.0 ml, 82 mmol) was added to a solution of 3-cyclohexanepropanoic acid (5.00 g, 32 mmol) in chloroform (50 ml) at room temperature, and a small amount of dimethylformamide was added dropwise to the solution. The mixture was stirred at room temperature for four hours, and the reaction mixture was concentrated under reduced pressure. A solution of isopropylamine (1.70 g, 29 mmol) in methylene chloride (25 ml) and N-methylmorpholine (4.5 ml, 40 mmol) were added to a solution of the obtained oily matter in methylene chloride (25 ml) under ice-cooling. The mixture was stirred at room temperature overnight, water (50 ml) was added to the reaction mixture, and the whole was extracted with ethyl acetate (120 ml). The organic layer was washed with a 1 N hydrochloric acid (50 ml), a 0.1 N aqueous sodium hydroxide solution (50 ml) and saturated brine (20 ml) successively and dehydrated with anhydrous magnesium sulfate. Ethyl acetate was evaporated under reduced pressure to give 6.00 g (95%) of the target compound.

IR (KBr) 3304, 2923, 2851, 1637, 1547, 1449 cm$^{-1}$ (b) N-Isopropyl-3-cyclohexyl-1-propylamine hydrochloride (Reference compound No. 23-1)

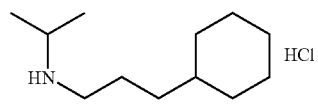

A solution of N-isopropyl-3-cyclohexylpropanamide (5.60 g, 29 mmol) in diethyl ether (60 ml) was added dropwise to a solution of lithium aluminum hydride (1.40 g, 38 mmol) in diethyl ether (75 ml) under ice-cooling. The mixture was stirred at room temperature for 2.5 hours, then water (1.3 ml), a 4 N aqueous sodium hydroxide solution (1.3 ml) and water (3.9 ml) were added to the reaction mixture successively under ice-cooling, and the whole was stirred at room temperature overnight. The reaction mixture was filtered, and the filtrate was concentrated under reduced pressure. 2 N hydrochloric acid (28 ml) was added to a solution of the obtained oily matter in ethanol (100 ml) at room temperature, and the whole was concentrated under reduced pressure. Ethanol and diethyl ether were added to the obtained oily matter, and the resulting insoluble matter was filtered off. The filtrate was concentrated under reduced pressure, and the obtained oily matter was treated in the same manner to filter off the insoluble matter. The obtained insoluble matters were combined and washed with ethyl acetate to give 1.20 g (19%) of the target compound.

IR (KBr) 3100-2530, 1449 cm$^{-1}$

EXAMPLE 1

3-Acetyl-2-[2-(3-(N-hydroxy-N-methylamino)propoxy)-5-methoxyphenyl]benzothiazoline hydrochloride (Compound No. 1-1)

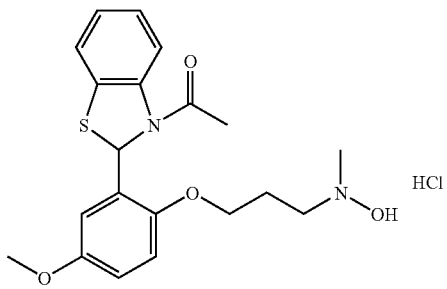

Potassium carbonate (590 mg, 4.25 mmol) and sodium iodide (530 mg, 3.54 mmol) were added to a solution of 3-acetyl-2-[2-(3-bromopropoxy)-5-methoxyphenyl]benzothiazoline (497 mg, 1.18 mmol) and N-methylhydroxylamine hydrochloride (209 mg, 2.36 mmol) in anhydrous DMF (6 ml) at room temperature. The mixture was stirred at 60° to 70° C. for three hours and then cooled to room temperature, water (50 ml) was added to the reaction mixture, and the whole was extracted with ethyl acetate (70 ml). The organic layer was washed with water twice and saturated brine successively and dehydrated with anhydrous sodium sulfate, ethyl acetate was evaporated under reduced pressure, and the obtained oily matter was purified by silica gel column chromatography (mobile phase:hexane/ethyl acetate=2/1). Ethyl acetate (2 ml) was added to the obtained oily matter, and a 4 N solution (5 ml) of hydrogen chloride in ethyl acetate was added thereto with stirring under ice cooling. The mixture was stirred at the temperature for five minutes, and the solvent was evaporated under reduced pressure. Hexane and ethyl acetate was added to the obtained oily matter, the mixture was stirred, and the precipitated solid was filtered off and dried under reduced pressure to give 331 mg (66%) of the target compound.

IR (KBr) 3416, 1672, 1499, 1466, 1381, 1209, 1041, 750 cm$^{-1}$

Similarly

3-Acetyl-2-[2-(3-(N-(2-hydroxyethyl)-N-methylamino)propoxy)-5-methoxyphenyl]benzothiazoline hydrochloride (Compound No. 1-2)

Yield: quantitatively
IR (neat) 3325, 2957, 2604, 1669, 1497, 1466, 1382, 1280, 1211, 1061, 752 cm$^{-1}$ 3-Acetyl-2-[2-(3-(N,N-bis(2-hydroxyethyl)amino)propoxy)-5-methoxyphenyl]benzothiazoline hydrochloride (Compound No. 1-3)

Yield: 91%
IR (KBr) 3331, 2958, 2586, 1664, 1498, 1467, 1369, 1318, 1279, 1244, 1213, 1049, 754 cm$^{-1}$ 3-Acetyl-2-[2-(3-(N-benzyl-N-(2-hydroxyethyl)amino)propoxy)-5-methoxyphenyl]benzothiazoline hydrochloride (Compound No. 1-4)

Yield: 94%
IR (neat) 3308, 2955, 2596, 1671, 1497, 1466, 1382, 1280, 1242, 1211, 1046, 751 cm$^{-1}$ 3-Acetyl-2-[2-(3-(N-(cyclohexylmethyl)-N-(2-hydroxyethyl)amino)-propoxy)-5-methoxyphenyl]benzothiazoline hydrochloride (Compound No. 1-5)

Yield: 76%
IR (neat) 3305, 2930, 2601, 1672, 1497, 1466, 1382, 1279, 1211, 1052, 754 cm$^{-1}$ 3-Acetyl-2-[2-(3-(N-(2-hydroxyethyl)-N-(3-phenylpropyl)amino)-propoxy)-5-methoxyphenyl]benzothiazoline hydrochloride (Compound No. 1-6)

Yield: 56%
IR (neat) 3306, 2952, 2588, 1672, 1497, 1466, 1280, 1243, 1211, 1048, 751 cm$^{-1}$ 3-Acetyl-2-[2-(3-(N-(2-hydroxyethyl)-N-(2-phenyloxyethyl)amino)-propoxy)-5-methoxyphenyl]benzothiazoline hydrochloride (Compound No. 1-7)

Yield: 53%
IR (neat) 3306, 2955, 2582, 1668, 1598, 1497, 1466, 1430, 1382, 1280, 1211, 1049, 752 cm$^{-1}$ 3-Acetyl-2-[2-(3-(N-(cyclopropylmethyl)-N-(2-hydroxyethyl)amino)-propoxy)-5-methoxyphenyl]benzothiazoline hydrochloride (Compound No. 1-8)

Yield: 73%
IR (neat) 3306, 2957, 2589, 1667, 1498, 1467, 1383, 1280, 1211, 1045, 754 cm$^{-1}$ 3-Acetyl-2-[2-(3-(N-(2-hydroxyethyl)-N-isopropylamino)propoxy)-5-methoxyphenyl]benzothiazoline hydrochloride (Compound No. 1-9)

Yield: 78%
IR (neat) 3307, 2955, 2835, 1668, 1497, 1466, 1383, 1280, 1211, 1055, 752 cm$^{-1}$ 3-Acetyl-2-[2-(3-(N-methylamino)propoxy)-5-methoxyphenyl]-benzothiazoline hydrochloride (Compound No. 1-10).

Yield: 43%
IR (neat) 3416, 2958, 2723, 1672, 1577, 1499, 1465, 1429, 1381, 1323, 1280, 1242, 1210, 1040, cm$^{-1}$ 3-Acetyl-2-[2-(3-(N-(ethoxycarbonylmethyl)-N-methylamino)-propoxy)-5-methoxyphenyl]benzothiazoline hydrochloride (Compound No. 1-11)

Yield: 80%
IR (neat) 3400, 2941, 2460, 1748, 1673, 1497, 1467, 1381, 1279, 1211, 1048, 752 cm$^{-1}$ 3-Acetyl-2-[2-(3-(N-(aminocarbonylmethyl)-N-methylamino)propoxy)-5-methoxyphenyl]benzothiazoline hydrochloride (Compound No. 1-12)

Yield: 85%
IR (neat) 3324, 3152, 3010, 2958, 1685-1680, 1498, 1466, 1382, 1324, 1279, 1243, 1211, 1047, 751 cm$^{-1}$ 3-Acetyl-2-[2-(3-(N—(N,N-dimethylaminocarbonylmethyl)-N-methylamino)propoxy)-5-methoxyphenyl]benzothiazoline hydrochloride (Compound No. 1-13)

Yield: 97%
IR (neat) 2938, 1664, 1498, 1465, 1382, 1279, 1211, 1046, 751 cm$^{-1}$ 3-Acetyl-2-[2-(3-(N-methoxy-N-methylamino)propoxy)-5-methoxyphenyl]benzothiazoline hydrochloride (Compound No. 1-14)

Yield: 59%

IR (KBr) 2948, 2300, 1684, 1500, 1464, 1384, 1284, 1212, 1038, 1013, 750 cm$^{-1}$

3-Acetyl-2-[2-(3-(N-(2-(N,N-dimethylamino)ethyl)-N-methylamino)-propoxy)-5-methoxyphenyl]benzothiazoline hydrochloride (Compound No. 1-15)

Yield: 59%
IR (KBr) 2961, 2623, 1668, 1466, 1381, 1279, 1242, 1210, 1040, 750 cm$^{-1}$ 3-Acetyl-2-[2-(3-(N,N-dipentylamino)propoxy)-5-methoxyphenyl]-benzothiazoline hydrochloride (Compound No. 1-16)

Yield: 91%
IR (neat) 2957, 2594, 1672, 1497, 1466, 1382, 1324, 1280, 1243, 1210, 1046, 752 cm$^{-1}$ 3-Acetyl-2-[2-(3-(N-benzyl-N-(2-methylthioethyl)amino)propoxy)-5-methoxyphenyl]benzothiazoline hydrochloride (Compound No. 1-17)

Yield: 43%
IR (neat) 2952, 2455, 1672, 1497, 1466, 1381, 1280, 1211, 1044, 750 cm$^{-1}$ 3-Acetyl-2-[2-(3-(N-(benzyloxycarbonylmethyl)-N-methylamino)-propoxy)-5-methoxyphenyl]benzothiazoline hydrochloride (Compound No. 1-18)

Yield: 50%
IR (neat) 2581, 1749, 1673, 1279, 1211, 807, 751, 699 cm$^{-1}$

3-Acetyl-2-[2-(3-(N-hydroxy-N-isopropylamino)propoxy)-5-methoxyphenyl]benzothiazoline (Compound No. 1-19)

Yield: 67%
IR (KBr) 3187, 2864, 1681, 1574, 1500, 1465, 1379, 1217 cm$^{-1}$

EXAMPLE 2

3-Acetyl-2-[2-(2-(N-(ethoxycarbonylmethyl)-N-methylamino)ethoxy)-5-methoxyphenyl]benzothiazoline hydrochloride (Compound No. 2-1)

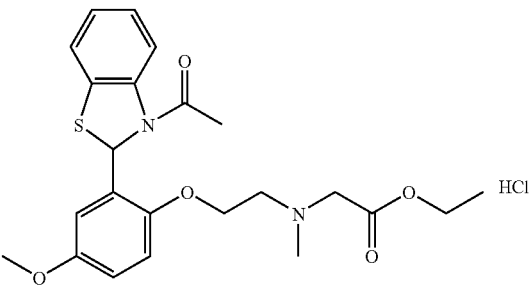

The target compound (261 mg, 44%) was obtained from 3-acetyl-2-[2-(3-bromoethoxy)-5-methoxyphenyl]benzothiazoline (500 mg) by a method similar to Example 1.
IR (neat) 2577, 1748, 1673, 1282, 1211, 1106, 809, 752 cm$^{-1}$

EXAMPLE 3

3-Acetyl-6-chloro-2-[2-(3-(N-(2-methoxyethyl)-N-n-propylamino)-propoxy)-5-methoxyphenyl]benzothiazoline hydrochloride (Compound No. 3-1)

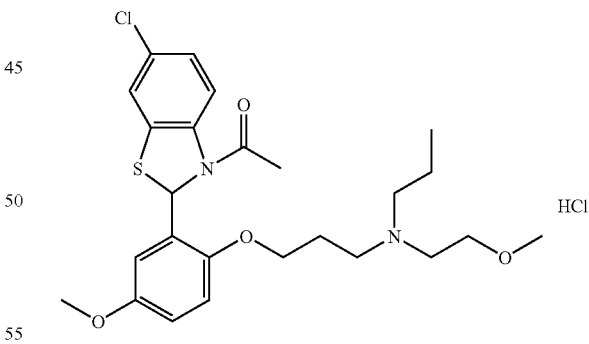

Potassium carbonate (229 mg, 1.64 mmol) and sodium iodide (493 mg, 3.27 mmol) were added to a solution of 3-acetyl-6-chloro-2-[2-(3-chloropropoxy)-5-methoxyphenyl]benzothiazoline (451 mg, 1.09 mmol) and N-(2-methoxyethyl)-n-propylamine (259 mg, 2.18 mmol) in anhydrous dimethylformamide at room temperature. The mixture was stirred at 60° to 70° C. for 3.5 hours, and then the reaction mixture was cooled to room temperature. Water (50 ml) was added to the reaction mixture, and the whole was extracted with ethyl acetate (70 ml). The organic layer was washed with water twice and saturated brine successively and dehydrated with anhydrous sodium sulfate, ethyl acetate was evaporated under reduced pressure, and the obtained oily matter was purified by silica gel column chromatography (mobile phase: ethyl acetate). Chloroform (2 ml) was added to the obtained oily matter, and a 4 N solution (5 ml) of hydrogen chloride in ethyl acetate was added thereto with stirring under ice-cooling. The mixture was stirred at the temperature for five minutes, and the solvent was evaporated under reduced pressure. Ethyl ether and ethyl acetate were added to the obtained oily matter, and the precipitated solid was filtered off and dried under reduced pressure to give 349 mg (60%) of the target compound.

IR (KBr) 2937, 2460, 1684, 1501, 1464, 1378, 1215, 1041, 811 cm$^{-1}$

Similarly

3-Acetyl-6-chloro-2-[2-(3-(N-(2-hydroxyethyl)-N-isopropylamino)-propoxy)-5-methoxyphenyl]benzothiazoline hydrochloride (Compound No. 3-2)

Yield: 66%
IR (KBr) 3288, 2605, 1684, 1420, 1380, 1217, 1056, 811, 745 cm$^{-1}$ 3-Acetyl-6-chloro-2-[2-(3-(N-(2-cyclopropylmethyl)-N-(2-hydroxyethyl)amino)propoxy)-5-methoxyphenyl]benzothiazoline hydrochloride (Compound No. 3-3)

Yield: 60%
IR (neat) 3307, 2955, 2593, 1674, 1498, 1464, 1378, 1210, 1059, 810, 754 cm$^{-1}$ 3-Acetyl-6-chloro-2-[2-(3-(N-cyclohexyl-N-(2-hydroxyethyl)amino)-propoxy)-5-methoxyphenyl]benzothiazoline hydrochloride (Compound No. 3-4)

Yield: 48%
IR (KBr) 3297, 2596, 1685, 1214, 1060, 1043, 811 cm$^{-1}$

3-Acetyl-6-chloro-2-[2-(3-(N-ethyl-N-(2-hydroxyethyl)amino)propoxy)-5-methoxyphenyl]benzothiazoline hydrochloride (Compound No. 3-5)

Yield: 48%

IR (KBr) 3306, 2648, 1684, 1217, 1094, 1040, 811 cm$^{-1}$

3-Acetyl-6-chloro-2-[2-(3-(N-(1-ethylpropyl)-N-(2-hydroxyethyl)-amino)propoxy)-5-methoxyphenyl]benzothiazoline hydrochloride (Compound No. 3-6)

Yield: 30%
IR (KBr) 3288, 2971, 1683, 1497, 1464, 1378, 1282, 1212, 1061, 810 cm$^{-1}$ 3-Acetyl-6-chloro-2-[2-(3-(N-(3-hydroxypropyl)-N-isopropylamino)-propoxy)-5-methoxyphenyl]benzothiazoline hydrochloride (Compound No. 3-7)

Yield: 48%
IR (KBr) 3388, 1684, 1216, 1056, 811 cm$^{-1}$

3-Acetyl-6-chloro-2-[2-(3-(N-(2-hydroxy-2-methylpropyl)-N-isopropylamino)propoxy)-5-methoxyphenyl]benzothiazoline hydrochloride (Compound No. 3-8)

Yield: 63%
IR (neat) 3305, 2973, 2834, 1674, 1497, 1464, 1378, 1281, 1210, 1057, 810, 754 cm$^{-1}$ 3-Acetyl-6-chloro-2-[2-(3-(N-(2-hydroxyethyl)amino)propoxy)-5-methoxyphenyl]benzothiazoline hydrochloride (Compound No. 3-9)

Yield: 46%
IR (KBr) 3368, 2952, 2831, 1684, 1500, 1464, 1378, 1217, 1042, 814 cm$^{-1}$ 3-Acetyl-6-chloro-2-[2-(3-(N-(2-hydroxyethyl)-N-n-propylamino)-propoxy)-5-methoxyphenyl]benzothiazoline hydrochloride (Compound No. 3-10)

Yield: 78%
IR (neat) 3312, 2963, 2619, 1672, 1497, 1463, 1377, 1210, 1045, 810, 751 cm$^{-1}$ 3-Acetyl-6-chloro-2-[2-(3-(N-(2-hydroxyethyl)-N-(2-methylpropyl)-amino)propoxy)-5-methoxyphenyl]benzothiazoline hydrochloride (Compound No. 3-11)

Yield: 61%
IR (KBr) 3308, 2600, 1684, 1213, 1094, 1057, 811 cm$^{-1}$

3-Acetyl-6-chloro-2-[2-(3-((2S)-2-hydroxymethylazolan-1-yl)propoxy)-5-methoxyphenyl]benzothiazoline hydrochloride (Compound No. 3-12)

Yield: 60%
IR (KBr) 3346, 2600-2500, 1684, 1215, 1041, 811 cm$^{-1}$

3-Acetyl-6-chloro-2-[2-(3-((2S)-2-methoxymethylazolan-1-yl)propoxy)-5-methoxyphenyl]benzothiazoline hydrochloride (Compound No. 3-13)

Yield: 64%
IR (KBr) 3424, 2600-2400, 1676, 1210, 1094, 1044, 810 cm$^{-1}$

3-Acetyl-6-chloro-2-[2-(3-((3S)-hydroxyazolan-1-yl)propoxy)-5-methoxyphenyl]benzothiazoline hydrochloride (Compound No. 3-14)

Yield: 92%
IR (neat) 3306, 2956, 2594, 1673, 1498, 1463, 1378, 1211, 1044, 810, 755 cm$^{-1}$ 3-Acetyl-6-chloro-2-[2-(3-((2S)-methoxycarbonylazolan-1-yl)propoxy)-5-methoxyphenyl]benzothiazoline hydrochloride (Compound No. 3-15)

Yield: 82%
IR (KBr) 2545, 1747, 1678, 1236, 1210, 1044, 810 cm$^{-1}$

3-Acetyl-2-[2-(3-(N-n-butyl-N-(2-hydroxyethyl)amino)propoxy)-5-methoxyphenyl]-6-chlorobenzothiazoline hydrochloride (Compound No. 3-16)

Yield: 95%
IR (neat) 3306, 2960, 2604, 1673, 1498, 1464, 1378, 1210, 1058, 810, 755 cm$^{-1}$

3-Acetyl-6-chloro-2-[2-(3-(N-cyclopentyl-N-(2-hydroxyethyl)amino)-propoxy)-5-methoxyphenyl]benzothiazoline hydrochloride (Compound No. 3-17)

Yield: 49%
IR (neat) 3306, 2957, 2594, 1675, 1497, 1464, 1377, 1282, 1210, 1046, 810, 754 cm$^{-1}$

3-Acetyl-6-chloro-2-[2-(3-(N-(2-hydroxy-1-(hydroxymethyl)ethyl)-amino)propoxy)-5-methoxyphenyl]benzothiazoline hydrochloride (Compound No. 3-18)

Yield: 72%
IR (KBr) 3315, 2950, 1680, 1500, 1464, 1377, 1211, 1043, 809 cm$^{-1}$ 3-Acetyl-6-chloro-2-[2-(3-(N-cyclopropyl-N-(2-hydroxyethyl)amino)-propoxy)-5-methoxyphenyl]benzothiazoline hydrochloride (Compound No. 3-19)

Yield: 87%
IR (neat) 3326, 2956, 2579, 2485, 1674, 1498, 1464, 1378, 1211, 1042, 810, 755 cm$^{-1}$

3-Acetyl-6-chloro-2-[2-(3-(N-(1,1-dimethyl-2-hydroxyethyl)amino)-prop oxy)-5-methoxyphenyl]benzothiazoline hydrochloride (Compound No. 3-20)

Yield: 82%
IR (KBr) 3210, 2958, 2865, 1679, 1501, 1463, 1378, 1298, 1211, 1049, 808 cm$^{-1}$

3-Acetyl-6-chloro-2-[2-(3-(N-(2-hydroxyethyl)-N-(3-methylbutyl)-amino)propoxy)-5-methoxyphenyl]benzothiazoline hydrochloride (Compound No. 3-21)

Yield: 80%
IR (neat) 3304, 2958, 2596, 1676, 1498, 1464, 1378, 1281, 1210, 1094, 810, 754 cm$^{-1}$

3-Acetyl-6-chloro-2-[2-(3-(N-((1S)-2-hydroxy-1-isopropylethyl)amino)-propoxy)-5-methoxyphenyl]benzothiazoline hydrochloride (Compound No. 3-22)

Yield: 72%
IR (neat) 3334, 2458, 1673, 1211, 1058, 1045, 810 cm$^{-1}$

3-Acetyl-6-chloro-2-[2-(3-(N-ethyl-N-isopropylamino)propoxy)-5-methoxyphenyl]benzothiazoline hydrochloride (Compound No. 3-23)

Yield: 88%
IR (KBr) 2943, 2643, 1673, 1573, 1498, 1464, 1378 cm$^{-1}$

3-Acetyl-6-chloro-2-[2-(3-(N-hydroxy-N-isopropylamino)propoxy)-5-methoxyphenyl]benzothiazoline (Compound No. 3-24)

Yield: 79%
IR (KBr) 3418, 2943, 2643, 1673, 1573, 1498, 1464, 1378 cm$^{-1}$

3-Acetyl-6-chloro-2-[2-(3-(N-isopropyl-N-(2-methoxyethyl)amino)-propoxy)-5-methoxyphenyl]benzothiazoline hydrochloride (Compound No. 3-25)

Yield: 81%
IR (neat) 2466, 1673, 1210, 1116, 1045, 810 cm$^{-1}$

3-Acetyl-2-[2-(3-(N-benzyl-N-isopropylamino)propoxy)-5-methoxyphenyl]-6-chlorobenzothiazoline hydrochloride (Compound No. 3-26)

Yield: 89%
IR (neat) 2942, 2498, 1674, 1497, 1464, 1377, 1210, 1045, 810, 752 cm$^{-1}$

3-Acetyl-6-chloro-2-[2-(3-(N-cyclohexyl-N-isopropylamino)propoxy)-5-methoxyphenyl]benzothiazoline hydrochloride (Compound No. 3-27)

Yield: 57%.
IR (neat) 2939, 2487, 1674, 1497, 1464, 1377, 1210, 1052, 810, 752 cm$^{-1}$

3-Acetyl-6-chloro-2-[2-(3-(N-isopropylamino)propoxy)-5-methoxyphenyl]benzothiazoline hydrochloride (Compound No. 3-28)

Yield: 71%
IR (KBr) 2964, 2776, 2450, 1680, 1499, 1462, 1377, 1211, 1054, 811 cm$^{-1}$

3-Acetyl-6-chloro-2-[2-(3-(N-isobutyl-N-(2-methoxyethyl)amino)-propoxy)-5-methoxyphenyl]benzothiazoline hydrochloride (Compound No. 3-29)

Yield: 79%
IR (neat) 2592, 1674, 1210, 1117, 1043, 810 cm$^{-1}$

3-Acetyl-6-chloro-2-[2-(3-(N-ethyl-N-(2-methoxyethyl)amino)-propoxy)-5-methoxyphenyl]benzothiazoline hydrochloride (Compound No. 3-30)

Yield: 81%
IR (neat) 2600-2400, 1674, 1210, 1114, 1046, 810 cm$^{-1}$

3-Acetyl-2-[2-(3-(N-(2-benzyloxyethyl)-N-isopropylamino)propoxy)-5-methoxyphenyl]-6-chlorobenzothiazoline hydrochloride (Compound No. 3-31)

Yield: 73%
IR (neat) 2500-2400, 1674, 1210, 1106, 1046, 810, 751, 700 cm$^{-1}$

3-Acetyl-6-chloro-2-[2-(3-(N-(3-cyclohexylpropyl)-N-isopropylamino)-propoxy)-5-methoxyphenyl]benzothiazoline hydrochloride (Compound No. 3-32)

Yield: 61%
IR (KBr) 2922, 2608, 1676, 1498, 1464, 1378, 1210 cm$^{-1}$

3-Acetyl-6-chloro-2-[2-(3-(N-(2-ethoxyethyl)-N-isopropylamino)-propoxy)-5-methoxyphenyl]benzothiazoline hydrochloride (Compound No. 3-33)

IR (neat) 2600-2400(b), 1675, 1210, 1108, 1046, 810 cm$^{-1}$

3-Acetyl-6-chloro-2-[2-(3-(N-(cyclopropylmethyl)-N-(2-methoxyethyl)amino)propoxy)-5-methoxyphenyl]benzothiazoline hydrochloride (Compound No. 3-34)

Yield: 73%
IR (neat) 2936, 2588, 1676, 1499, 1464, 1377, 1210, 1040, 810 cm$^{-1}$

3-Acetyl-2-[2-(3-(N,N-bis(2-ethoxyethyl)amino)propoxy)-5-methoxyphenyl]-6-chlorobenzothiazoline hydrochloride (Compound No. 3-35)

Yield: 99%
IR (neat) 2973, 2878, 2459, 1674, 1498, 1464, 1378, 1210, 1118, 1047, 810, 754 cm$^{-1}$

3-Acetyl-6-chloro-2-[2-(3-(N-isopropyl-N-(2-methoxybenzyl)amino)-propoxy)-5-methoxyphenyl]benzothiazoline hydrochloride (Compound No. 3-36)

Yield: 45%
IR (neat) 2941, 2506, 1675, 1605, 1590, 1498, 1464, 1378, 1282, 1050, 754 cm$^{-1}$

3-Acetyl-6-chloro-2-[2-(3-(N-isopropyl-N-(pyridyl-2-ylmethyl)amino)-propoxy)-5-methoxyphenyl]benzothiazoline hydrochloride (Compound No. 3-37)

Yield: 64%
IR (neat) 2961, 2457, 2062, 1674, 1618, 1497, 1464, 1379, 1282, 1212, 1056, 754 cm$^{-1}$

3-Acetyl-6-chloro-2-[2-(3-(N-(furan-2-ylmethyl)-N-isopropylamino)-propoxy)-5-methoxyphenyl]benzothiazoline hydrochloride (Compound No. 3-38)

Yield: 67%
IR (neat) 2943, 2495, 1675, 1574, 1498, 1464, 1378, 1211, 810, 751 cm$^{-1}$

3-Acetyl-6-chloro-2-[2-(3-(N-isopropyl-N-(1,3-thiazol-2-ylmethyl)-amino)propoxy)-5-methoxyphenyl]benzothiazoline hydrochloride (Compound No. 3-39)

Yield: 38%
IR (neat) 2941, 2496, 1668, 1574, 1498, 1465, 1378, 1282, 1210, 1054, 809 cm$^{-1}$

EXAMPLE 4

3-Acetyl-2-[2-(3-(N-hydroxy-N-isopropylamino)propoxy)-5-methoxyphenyl]-5-trifluoromethylbenzothiazoline (Compound No. 4-1)

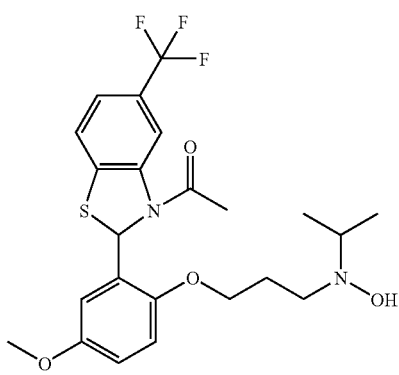

The target compound (231 mg, 53%) was obtained from 3-acetyl-2-[2-(3-chloropropoxy)-5-methoxyphenyl]-5-trifluoromethylbenzothiazoline (400 mg) by a method similar to Example 3.
IR (KBr) 3200, 2972, 1675, 1596, 1501 cm$^{-1}$
Similarly

3-Acetyl-2-[2-(3-(N-(2-hydroxyethyl)-N-isopropylamino)propoxy)-5-methoxyphenyl]-5-trifluoromethylbenzothiazoline hydrochloride (Compound No. 4-2)

Yield: 50%
IR (KBr) 3338, 2970, 2632, 1680, 1595, 1499, 1430, 1323 cm$^{-1}$

EXAMPLE 5

3-Acetyl-5-chloro-2-[2-(3-(N-hydroxy-N-isopropylamino)propoxy)-5-methoxyphenyl]benzothiazoline hydrochloride (Compound No. 5-1)

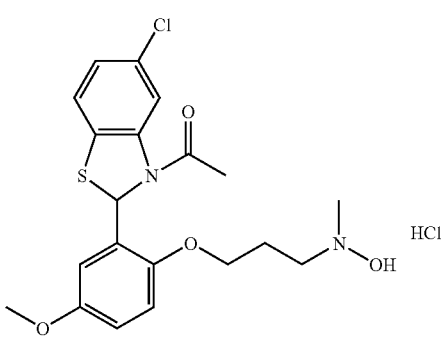

The target compound (376 mg, 58%) was obtained from 3-acetyl-5-chloro-2-[2-(3-chloropropoxy)-5-methoxyphenyl]-benzothiazoline (551 mg) by a method similar to Example 3.

IR (neat) 2944, 2834, 1680, 1497, 1463, 1408, 1379, 1282, 1211, 754 cm$^{-1}$

Similarly

3-Acetyl-5-chloro-2-[2-(3-(N-isopropyl-N-(2-methoxyethyl)amino)-propoxy)-5-methoxyphenyl]benzothiazoline hydrochloride (Compound No. 5-2)

Yield: 87%
IR (neat) 2937, 2619, 2494, 1682, 1497, 1463, 1408, 1380, 1323, 1282, 1240, 1106, 1043, 754 cm$^{-1}$ 3-Acetyl-5-chloro-2-[2-(3-(N-(2-hydroxyethyl)-N-isopropylamino)-prop oxy)-5-methoxyphenyl]benzothiazoline hydrochloride (Compound No. 5-3)

Yield: 92%
IR (neat) 3304, 2953, 2624, 1678, 1498, 1463, 1380, 1282, 1211, 1055, 754 cm$^{-1}$ 3-Acetyl-5-chloro-2-[2-(3-(N-(2-hydroxyethyl)-N-n-propylamino)-propoxy)-5-methoxyphenyl]benzothiazoline hydrochloride (Compound No. 5-4)

Yield: 65%
IR (KBr) 3347, 2965, 2624, 1680, 1499, 1464, 1379, 1283, 1211, 1053, 807 cm$^{-1}$

EXAMPLE 6

3Acetyl-6-chloro 2-[2-(2-(N-hydroxy-N-isopropylamino)ethoxy)-5-methoxyphenyl]benzothiazoline (Compound No. 6-1)

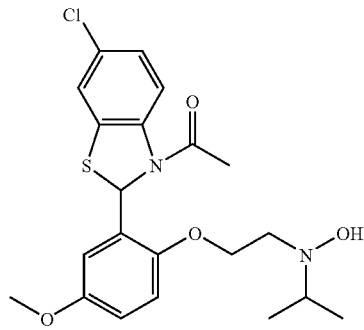

The target compound (234 mg, 59%) was obtained from 3-acetyl-6-chloro-2-[2-(2-bromoethoxy)-5-methoxyphenyl]-benzothiazoline (400 mg) by a method similar to Example 3.

IR (KBr) 3233, 2971, 1679, 1592, 1574, 1495, 1463, 1378, 1210, 1052, 810, 756 cm$^{-1}$

3-Acetyl-6-chloro-2-[2-(2-(N-(2-hydroxyethyl)-N-isopropylamino)-ethoxy)-5-methoxyphenyl]benzothiazoline hydrochloride (Compound No. 6-2)

Yield: 76%
IR (neat) 3306, 2951, 2614, 1676 cm$^{-1}$

3-Acetyl-6-chloro-2-[2-(2-(N-((1S)-2-hydroxy-1-isopropylethyl)amino)-ethoxy)-5-methoxyphenyl] benzothiazoline hydrochloride (Compound No. 6-3)

Yield: 75%
IR (neat) 3322, 2800-2600, 1674, 1210, 1095, 810 cm$^{-1}$

EXAMPLE 7

3-Acetyl-6-chloro-2-[2-(3-(N-hydroxy-N-isopropylamino)-1-methylpropoxy)-5-methoxyphenyl]benzothiazoline (Compound No. 7-1)

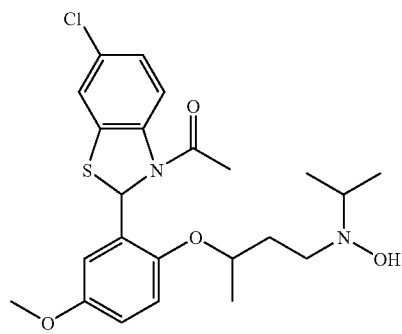

The target compound (397 mg, 28%) was obtained from 3-acetyl-6-chloro-2-[2-(1-methyl-3-p-toluenesulfonyloxypropoxy)-5-methoxyphenyl]benzothiazoline (1.70 g) by a method similar to Example 3.

IR (KBr) 3280, 2975, 2935, 2835, 1679, 1573, 1494, 1465, 1377, 1210, 810, 756 cm$^{-1}$

Similarly

3-Acetyl-6-chloro-2-[2-(3-(N-(2-hydroxyethyl)-N-isopropylamino)-1-methylpropoxy)-5-methoxyphenyl]benzothiazoline hydrochloride (Compound No. 7-2)

Yield: 40%
IR (neat) 3317, 2975, 2630, 1677, 1574, 1495, 1465, 1377, 1209, 1040, 810 cm$^{-1}$

EXAMPLE 8

3-Acetyl-2-[2-(3-(N-isopropyl-N-(2-methoxyethyl)amino)propoxy)-5-methoxyphenyl]benzothiazoline hydrochloride (Compound No. 8-1)

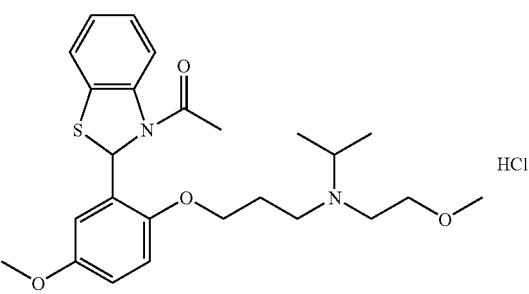

The target compound (474 mg, 81%) was obtained from 3-acetyl-2-[2-(3-chloropropoxy)-5-methoxyphenyl]benzothiazoline (500 mg) by a method similar to Example 3.

IR (neat) 2934, 2834, 2454, 1674, 1577, 1498, 1466, 1380, 1279, 1210, 1116, 1044, 751 cm$^{-1}$ Similarly 3-Acetyl-2-[2-(3-(N-(2-ethoxyethyl)-N-isopropylamino)propoxy)-5-methoxyphenyl]benzothiazoline hydrochloride (Compound No. 8-2)

Yield: 76%
IR (neat) 2968, 2871, 2479, 1674, 1592, 1577, 1497, 1466 1322 cm$^{-1}$

EXAMPLE 9

(+)-3-Acetyl-6-chloro-2-[2-(3-(N-isopropyl-N-(2-methoxyethyl)amino)-propoxy)-5-methoxyphenyl]benzothiazoline hydrochloride (Compound No. 9-1)

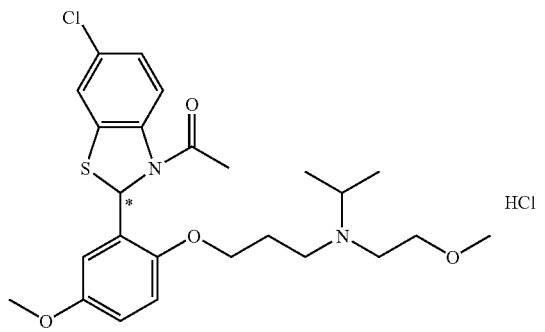

The target compound (1.53 g, 80%) was obtained from (+)-3-acetyl-6-chloro-2-[2-(3-chloropropoxy)-5-methoxyphenyl]-benzothiazoline (1.50 g) by a method similar to Example 3.

IR (KBr) 2938, 2835, 2607, 2495, 1677, 1499, 1465 cm$^{-1}$

Similarly (+)-3-Acetyl-6-chloro-2-[2-(3-(N-(2-hydroxyethyl)-N-isopropylamino)-propoxy)-5-methoxyphenyl]benzothiazoline hydrochloride (Compound No. 9-2)

Yield: 78%
IR (neat) 3307, 2939, 2609, 1687, 1497, 1465, 1376, 1211, 1061, 810 cm$^{-1}$ (+)-3-Acetyl-6-chloro-2-[2-(3-(N-(2-ethoxyethyl)-N-isopropylamino)-propoxy)-5-methoxyphenyl]benzothiazoline hydrochloride (Compound No. 9-3)

Yield: 49%
IR (neat) 2973, 2940, 2881, 2602, 2479, 1675, 1592, 1574, 1498, 1464 cm$^{-1}$ (+)-3-Acetyl-6-chloro-2-[2-(3-(N-isopropyl-N-(thiophen-2-ylmethyl)-amino)propoxy)-5-methoxyphenyl]benzothiazoline hydrochloride (Compound No. 9-4)

Yield: 14%
IR (neat) 2937, 2478, 1675, 1499, 1464, 1377, 1238, 1043, 809, 711 cm$^{-1}$ (+)-3-Acetyl-6-chloro-2-[2-(3-(N-(furan-2-ylmethyl)-N-isopropylamino)propoxy)-5-methoxyphenyl]benzothiazoline hydrochloride (Compound No. 9-5)

Yield: 62%
IR (neat) 2970, 2471, 1677, 1499, 1465, 1347, 1210, 1043, 809, 747 cm$^{-1}$ (+)-3-Acetyl-6-chloro-2-[2-(3-((2S)-2-hydroxymethylazolan-1-yl)-propoxy)-5-methoxyphenyl]benzothiazoline hydrochloride (Compound No. 9-6)

Yield: 36%
IR (neat) 3331, 2951, 2619, 1674, 1465, 1348, 1239, 1043, 810 cm$^{-1}$ (+)-3-Acetyl-2-[2-(3-((2S)-2-aminocarbonylazolan-1-yl)propoxy)-5-methoxyphenyl]-6-chlorobenzothiazoline hydrochloride (Compound No. 9-7)

Yield: 60%
IR (neat) 3376, 2958, 1681, 1577, 1465, 1378, 1211, 1044, 810 cm$^{-1}$ (+)-3-Acetyl-6-chloro-2-[2-(3-((2S)-2-methoxycarbonylazolan-1-yl)-propoxy)-5-methoxyphenyl]benzothiazoline hydrochloride (Compound No. 9-8)

Yield: 71%
IR (neat) 2955, 2855, 2554, 1747, 1679, 1574, 1465, 1348, 1210, 1045, 810 cm$^{-1}$ (+)-3-Acetyl-6-chloro-2-[2-(3-((2S)-2-methoxymethylazolan-1-yl)-propoxy)-5-methoxyphenyl]benzothiazoline hydrochloride (Compound No. 9-9)

Yield: 70%
IR (neat) 2940, 2836, 2610, 1676, 1574, 1465, 1348, 1238, 1041, 810 cm$^{-1}$ (+)-3-Acetyl-6-chloro-2-[2-(3-(N-ethyl-N-isopropylamino)propoxy)-5-methoxyphenyl]benzothiazoline hydrochloride (Compound No. 9-10)

Yield: 19%
IR (KBr) 2962, 2640, 2492, 1677, 1500, 1465, 1377, 1210, 1045, 810 cm$^{-1}$ (+)-3-Acetyl-6-chloro-2-[2-(3-(N,N-diisopropylamino)propoxy)-5-methoxyphenyl]benzothiazoline hydrochloride (Compound No. 9-11)

Yield: 10%
IR (KBr) 2964, 2653, 1679, 1499, 1465, 1377, 1210, 1047, 810 cm$^{-1}$ (+)-3-Acetyl-6-chloro-2-[2-(3-(N-isopropyl-N-methylamino)propoxy)-5-methoxyphenyl]benzothiazoline hydrochloride (Compound No. 9-12)

Yield: 74%
IR (neat) 2965, 1681, 1498, 1465, 1376, 1211, 1047, 810 cm$^{-1}$ (+)-3-Acetyl-6-chloro-2-[2-(3-((2S)-2-dimethylaminocarbonylazolan-1-yl)-propoxy)-5-methoxyphenyl]benzothiazoline hydrochloride (Compound No. 9-13)

Yield: 67%
IR (KBr) 2954, 1656, 1574, 1464, 1379, 1159, 1042, 809 cm$^{-1}$ (+)-3-Acetyl-6-chloro-2-[2-(3-(N-(2-hydroxy-2-methylpropyl)-N-isopropylamino)propoxy)-5-methoxyphenyl]benzothiazoline hydrochloride (Compound No. 9-14)

Yield: 35%
IR (KBr) 3331, 2957, 2639, 1676, 1499, 1465, 1379, 1210, 1056, 810 cm$^{-1}$ (+)-3-Acetyl-6-chloro-2-[2-(3-(N-hydroxy-N-isopropylamino)-propoxy)-5-methoxyphenyl]benzothiazoline hydrochloride (Compound No. 9-15)

Yield: 16%
IR (KBr) 3347, 2942, 1678, 1499, 1465, 1378, 1210, 1044, 810 cm$^{-1}$ (+)-3-Acetyl-6-chloro-2-[2-(3-(N-(2-hydroxyethyl)-N-methylamino)-propoxy)-5-methoxyphenyl]benzothiazoline hydrochloride (Compound No. 9-16)

Yield: 51%
IR (KBr) 3319, 2957, 2633, 1676, 1500, 1465, 1377, 1210, 1050, 810 cm$^{-1}$

EXAMPLE 10

(−)-3-Acetyl-6-chloro-2-[2-(3-(N-isopropyl-N-(2-methoxyethyl)amino)-propoxy)-5-methoxyphenyl]benzothiazoline hydrochloride (Compound No. 10-1)

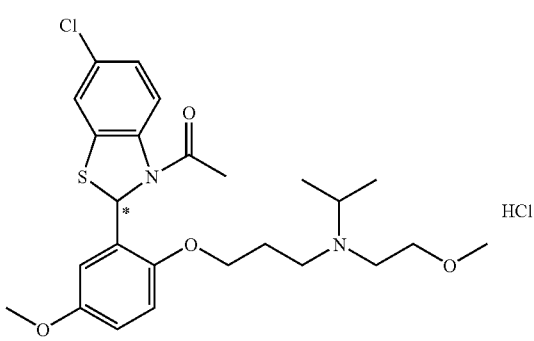

The target compound (790 mg, 56%) was obtained from (−)-3-acetyl-6-chloro-2-[2-(3-chloropropoxy)-5-methoxyphenyl]-benzothiazoline (1.09 g) by a method similar to Example 3.

IR (neat) 2939, 2487, 1675, 1498, 1464, 1210, 1116, 1042, 810 cm$^{-1}$

Similarly (−)-3-Acetyl-6-chloro-2-[2-(3-(N-(2-hydroxyethyl)-N-isopropylamino)-propoxy)-5-methoxyphenyl]benzothiazoline hydrochloride (Compound No. 10-2)

Yield: 60%
IR (KBr) 3294, 2936, 2591, 1688, 1497, 1465, 1374, 1283, 1211, 1061, 810 cm$^{-1}$ (−)-3-Acetyl-6-chloro-2-[2-(3-(N-(2-ethoxyethyl)-N-isopropylamino)-propoxy)-5-methoxyphenyl]benzothiazoline hydrochloride (Compound No. 10-3)

Yield: 61%
IR (neat) 2973, 2936, 2881, 2617, 2486, 1717, 1676, 1592, 1573, 1498, 1464 cm$^{-1}$

EXAMPLE 11

(+)-3-Acetyl-2-[2-(3-(N-(2-ethoxyethyl)-N-isopropylamino)propoxy)-5-methoxyphenyl]benzothiazoline hydrochloride (Compound No. 11-1)

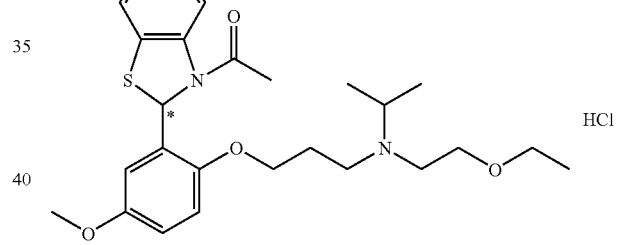

The target compound (677 mg, 52%) was obtained from (+)-3-acetyl-2-[2-(3-chloropropoxy)-5-methoxyphenyl]benzothiazoline (966 mg) by a method similar to Example 3.

IR (neat) 2968, 2611, 1967, 1675, 1592, 1577, 1497, 1466, 1380, 1278, 1210, 1160, 1107, 1046, 750 cm$^{-1}$ Similarly (+)-3-Acetyl-2-[2-(3-(N-isopropyl-N-(2-methoxyethyl)amino)-propoxy)-5-methoxyphenyl]benzothiazoline hydrochloride (Compound No. 11-2)

Yield: 95%
IR (neat) 2968, 2611, 1967, 1675, 1592, 1577, 1497, 1466, 1380, 1211, 1117, 1046, 751 cm$^{-1}$ (+)-3-Acetyl-2-[2-(3-(N-(2-hydroxyethyl)-N-isopropylamino)-propoxy)-5-methoxyphenyl]benzothiazoline hydrochloride (Compound No. 11-3)

Yield: 37%
IR (neat) 3321, 2963, 2621, 1672, 1592, 1497, 1382, 1211, 1047, 752 cm$^{-1}$

EXAMPLE 12

3'-Acetyl-2-[2-(3-(N,N-diethylamino)propoxy)-5-methoxyphenyl]-benzothiazoline hydrochloride (Compound No. 12-1)

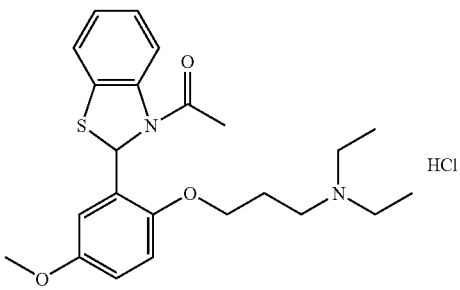

A solution of diisopropyl azodicarboxylate (470 mg, 2.32 mmol) in anhydrous tetrahydrofuran (1 ml) and a solution of 3-dimethylamino-1-propanol (0.35 ml, 2.32 mmol) in anhydrous tetrahydrofuran (1 ml) were added to a solution of 3-acetyl-2-(3-hydroxy-5-methoxyphenyl)benzothiazoline (700 mg, 2.32 mmol) and triphenylphosphine (609 mg, 2.32 mmol) in anhydrous tetrahydrofuran (4 ml) successively at room temperature, and the mixture was stirred for two days. The reaction mixture was concentrated, and the obtained oily matter was purified by silica gel column chromatography (mobile phase:ethyl acetate/methanol=20/1). Ethyl acetate (2 ml) was added to the obtained oily matter, and a 4 N solution (5 ml) of hydrogen chloride in ethyl acetate was added thereto with stirring under ice-cooling. The mixture was stirred at the temperature for 10 minutes, and the solvent was evaporated under reduced pressure to give 775 mg (74%) of the target compound.

IR (neat) 2944, 2581, 2468, 1672, 1498, 1466, 1382, 1279, 1244, 1210, 1044, 752 cm$^{-1}$

3-Acetyl-2-[2-(2-(dimethylamino)ethoxy)-5-methoxyphenyl]-benzothiazoline hydrochloride (Compound No. 12-2)

Yield: 62%
IR (KBr) 2967, 2370, 1676, 1496, 1464, 1382, 1351, 1283, 1210, 1030, 754 cm$^{-1}$

EXAMPLE 13

3-Acetyl-5-chloro-2-[2-(3-(dimethylamino)propoxy)-5-methoxyphenyl]benzothiazoline hydrochloride (Compound No. 13-1)

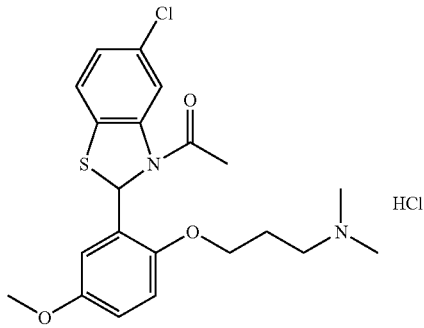

The target compound (407 mg, 50%) was obtained from 3-acetyl-5-chloro-2-(3-hydroxy-5-methoxyphenyl)benzothiazoline (600 mg) by a method similar to Example 7.

IR (KBr) 2961, 2572, 2510, 2449, 1683, 1496, 1464, 1376, 1315, 1211, 1042, 842 cm$^{-1}$

EXAMPLE 14

3-Acetyl-6-chloro-2-[2-(3-(N-ethoxycarbonylmethyl-N-isopropylamino)propoxy)-5-methoxyphenyl]benzothiazoline hydrochloride (Compound No. 14-1)

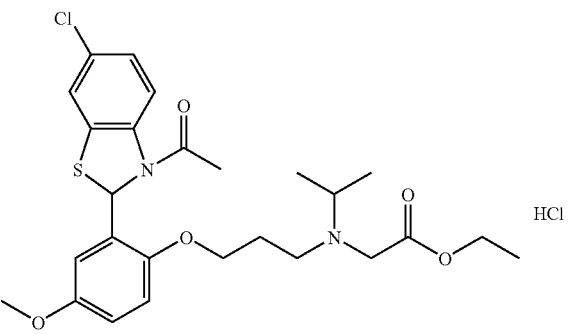

Potassium carbonate (299 mg, 2.16 mmol) and ethyl bromoacetate (0.13 ml, 1.13 mmol) were added to a solution of 3-acetyl-6-chloro-2-[2-(3-(N-isopropylamino)propoxy)-5-methoxyphenyl]benzothiazoline (compound described in Example 3) (474 mg, 1.08 mmol) in anhydrous dimethylformamide at room temperature. The mixture was stirred at room temperature for 1.5 hours, water (30 ml) was added to the reaction mixture, and the whole was extracted with diethyl ether (50 ml). The organic layer was washed with water twice and saturated brine successively and dehydrated with anhydrous magnesium sulfate. Diethyl ether was evaporated under reduced pressure, and the obtained oily matter was purified by silica gel column chromatography (mobile phase:hexane/ethyl acetate=1/1). Methanol (2 ml) was added to the obtained oily matter, and a 10% solution (5 ml) of hydrogen chloride in methanol was added thereto with stirring under ice-cooling. The mixture was stirred at the temperature for five minutes, and the solvent was evaporatd under reduced pressure to give 542 mg (90%) of the target compound.

IR (neat) 3406, 2942, 2458, 1747, 1674, 1498, 1464, 1378, 1210, 1042, 810, 753 cm$^{-1}$

EXAMPLE 15

2-[2-(3-(N-(2-Acetoxyethyl)-N-isopropylamino)propoxy)-5-methoxyphenyl]-3-acetyl-6-chlorobenzothiazoline hydrochloride (Compound No. 15-1)

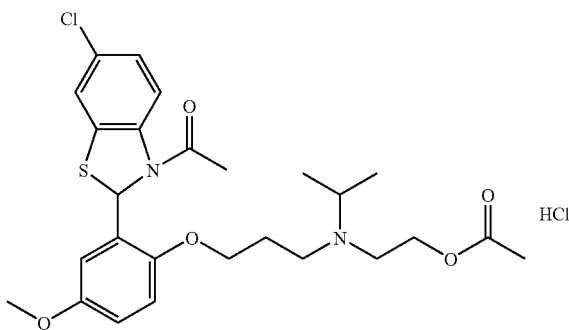

Acetic anhydride (0.26 ml, 2.91 mmol) was added to a solution of 3-acetyl-6-chloro-2-[2-(3-(N-(2-hydroxyethyl)-N-isopropylamino)-propoxy)-5-methoxyphenyl]benzothiazoline hydrochloride (300 m g, 0.58 mmol) in pyridine (0.47 ml, 5.80 mmol) under ice-cooling, and then the mixture was stirred at room temperature for two hours. A saturated aqueous sodium hydrogencarbonate solution (50 ml) was added to the reaction mixture, and the whole was extracted with ethyl acetate (50 ml). The ethyl acetate layer was washed with saturated brine (50 ml) and dehydrated with anhydrous magnesium sulfate, and ethyl acetate was evaporated under reduced pressure. The obtained oily matter was dissolved in ethyl acetate (1 ml), and then a 4 N solution (0.5 ml) of hydrogen chloride in ethyl acetate. The mixture was concentrated under reduced pressure to give 277 mg (92%) of the target compound.

IR (neat) 2604, 1745, 1676, 1211, 1050, 810 cm$^{-1}$

EXAMPLE 16

3-Acetyl-6-chloro-2-[2-(3-((2S)-2-acetoxymethylazolan-1-yl)-propoxy)-5-methoxyphenyl]benzothiazoline hydrochloride (Compound No. 16-1)

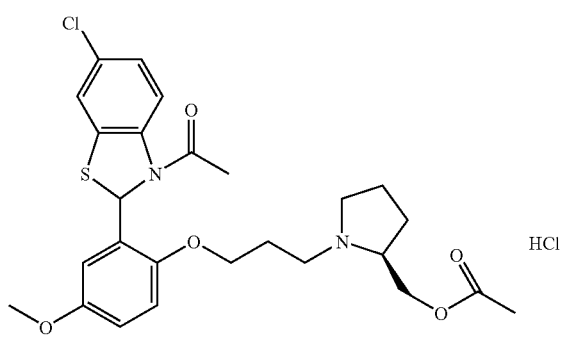

The target compound (556 mg, 95%) was obtained from 3-acetyl-6-chloro-2-[2-(3-((2S)-2-hydroxymethylazolan-1-yl)propoxy)-5-methoxyphenyl]benzothiazoline (500 mg) by a method similar to Example 15.

IR (KBr) 2594, 1745, 1676, 1210, 1045, 810 cm$^{-1}$

EXAMPLE 17

2-[2-(3-(N-Acetoxy-N-isopropylamino)propoxy)-5-methoxyphenyl]-3-acetyl-6-chlorobenzothiazoline p-toluenesulfonate (Compound No. 17-1)

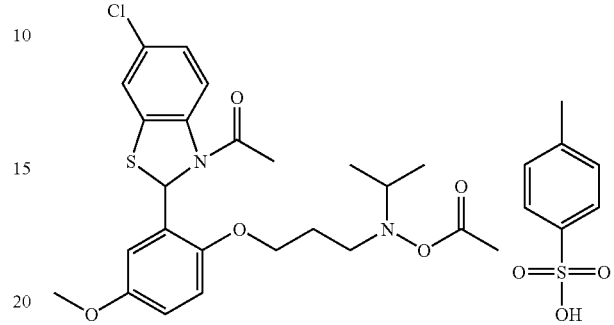

The target compound (266 mg, 60%) was obtained from 3-acetyl-6-chloro-2-[2-(3-(N-hydroxy-N-isopropylamino)propoxy)-5-methoxyphenyl]benzothiazoline (300 mg) by a method similar to Example 15.

IR (KBr) 3700-2000, 1805, 1722, 1679, 1573, 1499, 1464 cm$^{-1}$

EXAMPLE 18

3-Acetyl-6-chloro-2-[2-(3-(N-isopropyl-N-(2-phenylcarboxyethyl)-amino)propoxy)-5-methoxyphenyl]benzothiazoline hydrochloride (Compound No. 18-1)

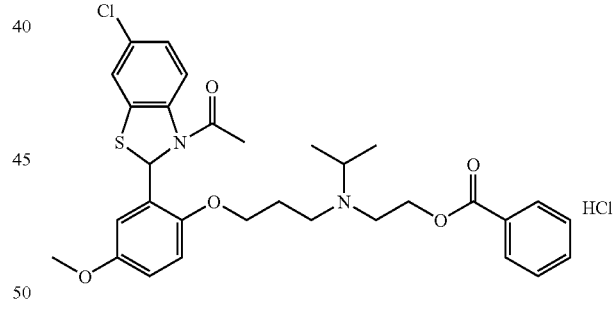

Benzoyl chloride (0.20 ml, 1.20 mmol) was added to a solution of 3-acetyl-6-chloro-2-[2-(3-(N-(2-hydroxyethyl)-N-isopropylamino)-propoxy)-5-methoxyphenyl]benzothiazoline hydrochloride (300 mg, 0.58 mmol) and pyridine (0.39 ml, 4.70 mmol) in methylene chloride (0.5 ml) under ice-cooling. The mixture was stirred at the temperature for two hours, then a saturated aqueous sodium hydrogencarbonate solution (50 ml) was added to the reaction mixture, and the whole was extracted with ethyl acetate (50 ml). The ethyl acetate layer was washed with a 10% aqueous citric acid solution (50 ml) and dehydrated with anhydrous magnesium sulfate, and ethyl acetate was evaporated under reduced pressure. The residue was purified by silica gel column chromatography (mobile phase:ethyl acetate/methanol=10/1). The obtained oily matter was dissolved in ethyl acetate (1 ml), and a 4 N solution (0.5 ml) of hydrogen chloride in ethyl acetate was added thereto under ice-cooling. The mixture was concentrated under reduced pressure to give 211 mg (62%) of the target compound.

IR (neat) 2456, 1721, 1674, 1272, 1210, 1110, 1044, 810, 754, 712 cm$^{-1}$

Similarly

3-Acetyl-2-[2-(3-(N-(2-tert-butylcarbonyloxyethyl)-N-isopropylamino)propoxy)-5-methoxyphenyl]-6-chlorobenzothiazoline hydrochloride (Compound No. 18-2)

Yield: quantitatively
IR (neat) 2494, 1730, 1678, 1465, 1282, 1158, 1045, 811 cm$^{-1}$

EXAMPLE 19

3-Acetyl-6-chloro-2-[2-(3-(N-isopropyl-N-(2-methoxyacetoxyethyl)-amino)propoxy)-5-methoxyphenyl]benzothiazoline hydrochloride (Compound No. 19-1)

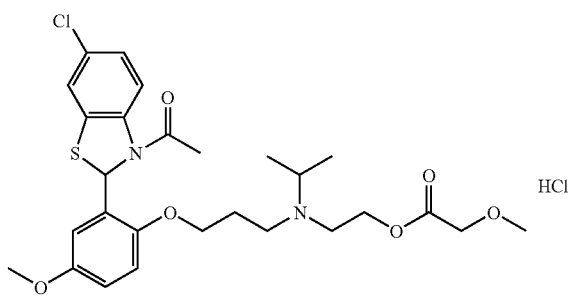

Methoxyacetyl chloride (0.08 ml, 0.87 mmol) was added to a solution of 3-acetyl-6-chloro-2-[2-(3-(N-(2-hydroxyethyl)-N-isopropylamino)propoxy)-5-methoxyphenyl]benzothiazoline hydrochloride (300 mg, 0.58 mmol) in triethylamine (0.41 ml, 2.90 mmol) and methylene chloride (1.0 ml) under ice-cooling. The mixture was stirred at room temperature for two hours, then water (50 ml) was added to the reaction mixture, and the whole was extracted with ethyl acetate (50 ml). The ethyl acetate layer was washed with saturated brine (50 ml) and dehydrated with anhydrous magnesium sulfate. Ethyl acetate was evaporated under reduced pressure, and the residue was purified by silica gel column chromatography (mobile phase: chloroform/methanol=50/1). The obtained oily matter was dissolved in ethyl acetate (1 ml), and then a 4 N solution (0.2 ml) of hydrogen chloride in ethyl acetate was added thereto under ice-cooling. The mixture was concentrated under reduced pressure to give 340 mg (quantitatively) of the target compound.

IR (neat) 2477, 1757, 1676, 1281, 1127, 1043, 810 cm$^{-1}$

EXAMPLE 20

3-Acetyl-6-chloro-2-[2-(3-(N-isopropyl-(N-(2-methoxymethyloxy-ethyl))amino)propoxy)-5-methoxyphenyl]benzothiazoline (Compound No. 20-1)

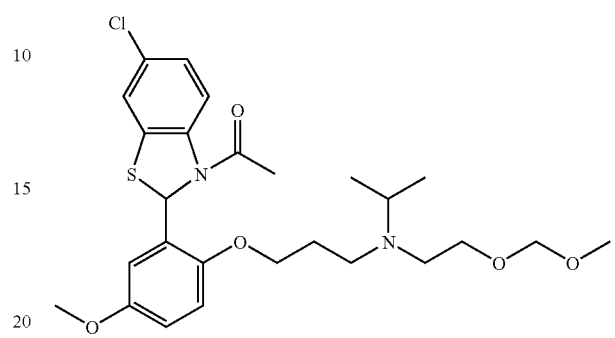

N,N-Diisopropylethylamine (0.18 ml, 1.01 mmol) and chlorodimethyl ether (0.05 ml, 0.55 mmol) were added to a solution of 3-acetyl-6-chloro-2-[2-(3-(N-(2-hydroxyethyl)-N-isopropylamino)-propoxy)-5-methoxyphenyl]benzothiazoline hydrochloride (235 mg, 0.46 mmol) in methylene chloride (2.0 ml) under ice-cooling. The mixture was stirred at room temperature for 3.5 hours, then a saturated aqueous sodium hydrogencarbonate solution (50 ml) was added to the reaction mixture, and the whole was extracted with ethyl acetate (50 ml). The ethyl acetate layer was washed with saturated brine (50 ml) and dehydrated with anhydrous magnesium sulfate, and ethyl acetate was concentrated under reduced pressure. The residue was purified by silica gel column chromatography (mobile phase: chloroform/methanol=20/1) to give 124 mg (52%) of the target compound.

IR (neat) 1682, 1234, 1151, 1108, 1043, 810 cm$^{-1}$
Similarly

3-Acetyl-6-chloro-2-[2-(3-(N-isopropyl-N-(2-(2-methoxyethoxymethoxy) -ethyl)amino)propoxy)-5-methoxyphenyl]benzothiazoline (Compound No. 20-2)

Yield: 71%
IR (neat) 1681, 1210, 1161, 1044, 810 cm$^{-1}$

Formulation Examples

General formulation examples of the present compound are shown below.

| 1) Tablet | |
|---|---|
| Formulation 1 in 100 mg | |
| Present compound | 1 mg |
| Lactose | 66.4 mg |
| Cornstarch | 20 mg |
| Calcium carboxymethylcellulose | 6 mg |
| Hydroxypropylcellulose | 4 mg |
| Magnesium stearate | 0.6 mg |

Tablets according to the formulation as above are coated with 2 mg/tablet of a coating agent (an ordinary coating agent such as hydroxypropylmethylcellulose, macrogol or silicone resin) to obtain desired coated tablets. (The same is applied to tablets mentioned below.) Desired tablets can be obtained by appropriately changing the amounts of the present compound and the additives.

| 2) Capsule | |
|---|---|
| Formulation 1 in 150 mg | |
| Present compound | 5 mg |
| Lactose | 145 mg |

Desired capsules can be obtained by appropriately changing the mixing ratio of the present compound to lactose.

Pharmacological Tests

1. κ opioid receptor agonist activity tests in GTP binding activity measurement system Jinmin Zhu et al. reported a method of evaluating agonist activities of drugs on a κ opioid receptor wherein guanosine 5'-triphosphate (GTP) radiolabelled with a human κ opioid receptor is used in J. Pharmaco. Exp. Ter., 282, 676-684 (1997). κ opioid receptor agonist activities (actions) of test compounds were evaluated according to the method described in the above-mentioned literature.

Preparation of Incubation Buffer

N-2-Hydroxyethylpiperazine-N'-2-ethanesulfonic acid (HEPES, 4.77 g), magnesium chloride hexahydrate (2.03 g), sodium chloride (5.84 g), disodium ethylenediaminediacetate (EDTA·2Na, 0.37 g), DL-dithiothreitol (DTT, 0.15 g) and bovine serum albumin (BSA, 1.0 g) were dissolved in ultrapure water, pH was adjusted to 7.4 with sodium hydroxide, and further ultrapure water was added to the mixture so that a total amount was one liter to prepare a incubation buffer.

Preparation of 10% Dimethyl Sulfoxide-incubation Buffer

Nine volume of the incubation buffer was added to one volume of dimethyl sulfoxide (DMSO) to prepare a 10% DMSO-incubation buffer.

Preparation of 50 mM Tris-hydrochloric Acid Buffer

Tris(hydroxymethyl)aminomethane hydrochloride (TRIZA-HCl, 66.1 g) and Tris(hydroxymethyl)aminomethane (TRIZA-Base, 9.7 g) were dissolved in ultrapure water so that a total amount was 10 liters to prepare a 50 mM Tris-hydrochloric acid buffer (pH 7.4).

Preparation of κ Receptor Membrane Preparation Solution

A human κ opioid receptor membrane preparation (100 unit/ml) was diluted 60 times with the incubation buffer under ice-cold to prepare a human κ opioid receptor membrane preparation solution. The membrane preparation solution was preserved under ice-cold.

Preparation of Test Compound Solution

A test compound was dissolved in 100% DMSO to prepare a $10^{-3}$ M test compound solution, and then the incubation buffer was added to the $10^{-3}$ M test compound solution to prepare a $10^{-4}$ M test compound solution. Next, the 10% dimethyl sulfoxide-incubation buffer was added to the $10^{-4}$ M test compound solution to prepare a $10^{-5}$ M, $10^{-6}$ M, $10^{-7}$ M, $10^{-8}$ M or $10^{-9}$ M test compound solution.

Preparation of Positive Control Drug ((−)-U-50488) Solution

A drug (−)-U50488 (J. Pharmacol. Exp. Ther., 224, 7-12 (1983)), which is known as a κ opioid receptor agonist, was used as a positive control drug in the tests.

(−)-U-50488 was dissolved in 100% DMSO to prepare a $10^{-3}$ M positive control drug solution, and then the incubation buffer was added to the $10^{-3}$ M positive control drug solution to prepare a $10^{-4}$ M positive control drug solution. Next, the 10% DMSO-incubation buffer was added to the $10^{-4}$ M positive control drug solution to prepare a $10^{-6}$ M positive control drug solution.

Preparation of Guanosine 5'-diphosphate (GDP) Solution

GDP was dissolved in ultrapure water to prepare a $10^{-3}$ M GDP solution, and the incubation buffer was added to the $10^{-3}$ M GDP solution to prepare a $10^{-6}$ M GDP solution.

Preparation of Radiolabelled Reagent $10^{-3}$ M [$^{35}$S]GTPγ S was diluted with the incubation buffer to prepare $10^{-9}$ M radiolabelled reagent.

Test Method

1. The incubation buffer (50 μl), the $10^{-5}$ M GDP solution (50 μl), the human κ opioid receptor membrane preparation solution (300 μl), the test compound solution and the $10^{-9}$ M radiolabelled reagent (50 μl) were put into a glass tube, and then the mixture was incubated at 30° C. for 60 minutes.
2. The 50 mM Tris-hydrochloric acid buffer (pH 7.4) was added to the mixture to stop the reaction, the reaction mixture was suction-filtered with a GF/B filter, and then the residue on the GF/B filter was washed with the 50 mM Tris-hydrochloric acid buffer (3 ml) three times.
3. The GF/B filter was air-dried, and then the residue on the GF/B filter was taken out with an antomatic dispenser and transferred into a vial.
4. Scintisol EX-H (5 ml) was introduced into the vial to prepare a sample solution, and then radioactivity in the sample solution was measured with a liquid scintillation counter for one minute. The radioactivity was expressed in "cpm" (counts per minute).

Calculation Formula of κ Opioid Receptor Agonist Activity

Each agonist activity of the test compound on the κ opioid receptor was expressed in [$^{35}$S]GTPγ S binding. % when [$^{35}$S]GTPγ S binding of $10^{-6}$ M (−)-U50488 was 100%. Namely, [35S]GTPγ S binding was calculated according to the following equation.

[$^{35}$S]GTPγ S binding %=[[$^{35}$S]GTPγ S binding of test compound (cpm)−[$^{35}$S]GTPγ S binding of solvent (cpm)]/[$^{35}$S]GTPγ S binding of positive control drug ($10^{-6}$ M (−)-U50488) (cpm)−[$^{35}$S]GTPγ S binding of solvent (cpm)]×100

Test Results

Table 1 shows [$^{35}$S]GTPγ S binding (κ opioid receptor agonist) activities (%) when test compounds (compound Nos. 3-2, 3-11, 3-12, 3-14, 3-25, 3-33, 3-38, 4-2, 5-3, 7-2, 8-1, 9-1, 9-2, 9-3, 9-4, 9-5, 9-10, 9-11, 9-12, 9-16, 10-1, 10-2, 10-3, 11-1, 11-3, 20-1 and 20-2) were used of which concentration was $10^{-9}$ M respectively, as examples of test results.

TABLE 1

| Test compound | [$^{35}$S]GTP γ S binding % |
|---|---|
| Compound No. 3-2 | 66.5 |
| Compound No. 3-11 | 53.7 |
| Compound No. 3-12 | 75.6 |
| Compound No. 3-14 | 59.8 |
| Compound No. 3-25 | 67.9 |
| Compound No. 3-33 | 75.8 |
| Compound No. 3-38 | 58.4 |
| Compound No. 4-2 | 65.1 |

TABLE 1-continued

| Test compound | [$^{35}$S]GTP γ S binding % |
|---|---|
| Compound No. 5-3 | 51.2 |
| Compound No. 7-2 | 62.9 |
| Compound No. 8-1 | 103.0 |
| Compound No. 9-1 | 93.2 |
| Compound No. 9-2 | 103.9 |
| Compound No. 9-3 | 117.5 |
| Compound No. 9-4 | 72.1 |
| Compound No. 9-5 | 132.5 |
| Compound No. 9-10 | 116.8 |
| Compound No. 9-11 | 55.0 |
| Compound No. 9-12 | 107.9 |
| Compound No. 9-16 | 57.2 |
| Compound No. 10-1 | 50.5 |
| Compound No. 10-2 | 65.8 |
| Compound No. 10-3 | 55.7 |
| Compound No. 11-1 | 66.8 |
| Compound No. 11-3 | 85.1 |
| Compound No. 20-1 | 65.1 |
| Compound No. 20-2 | 50.5 |

(The values in Table 1 are the average of duplicate once tests.)

As shown in Table 1, the present compounds exhibit excellent κ opioid receptor agonist activities (actions).

2. Antinociceptive Action Tests by Mouse Acetic Acid Writhing Method

A mouse acetic acid writhing method by Anderson et al. (Fed. Proc., 18, 412 (1985)) is widely used as a method of evaluating analgesic effects of drugs. Accordingly, antinociceptive action tests of test compounds were carried out using the mouse acetic acid writhing method, and analgesic effects of the test compounds were evaluated.

Preparation of 0.7% Acetic Acid Solution

Physiological saline was added to 99.7% acetic acid to prepare a 0.7% acetic acid solution.

Experimental Method

Twenty minutes after oral administration of the test compound (30 mg/kg), the 0.7% acetic acid solution was administered intraperitoneally in a rate of 0.1 ml per 10 g of mouse weight. Next, times of writhing exhibited 10 to 20 minutes after administering acetic acid were counted to measure its antinociceptive action.

Inhibition rates were calculated according to the following equation.

The antinociceptive action of the test compound was expressed in an inhibition rate to writhing numbers of a vehicle group.

Inhibition rate (%)=[1−(writhing numbers of drug administration group/writhing numbers of vehicle group)]×100

Test Results

Table 2 shows antinociceptive actions (inhibition rates (%) to writhing times of the vehicle group) of the test compounds (compound Nos. 3-2, 3-25, 3-33, 5-3, 7-2, 9-1, 9-2, 9-12, 9-3, 11-1, 20-1 and 20-2) as examples of test results.

TABLE 2

| Test compound | Inhibition rate (%) |
|---|---|
| Compound No. 3-2 | 76.1 |
| Compound No. 3-25 | 91.0 |
| Compound No. 3-33 | 99.5 |
| Compound No. 5-3 | 51.6 |
| Compound No. 7-2 | 70.0 |
| Compound No. 9-1 | 97.7 |

TABLE 2-continued

| Test compound | Inhibition rate (%) |
|---|---|
| Compound No. 9-2 | 81.2 |
| Compound No. 9-12 | 57.8 |
| Compound No. 9-3 | 100.0 |
| Compound No. 11-1 | 98.3 |
| Compound No. 20-1 | 94.8 |
| Compound No. 20-2 | 81.7 |

(The values in Table 2 are the average of seven samples.)

As shown in the above Table 2, the present compounds exhibit excellent antinociceptive actions in the antinociceptive action tests using the mouse acetic acid writhing method.

INDUSTRIAL APPLICABILITY

2-Phenylbenzothiazoline derivative or salts thereof (present compounds) have excellent κ opioid receptor agonist activities and antinociceptive actions. Accordingly, the present compounds are particularly useful as therapeutic agents for pain, pruritus and the like.

What is claimed is:

1. A method of treating pain or pruritis comprising administering to a patient in need thereof a pharmaceutically effective amount of a κ opioid receptor agonist comprising a compound having a chemical structure represented by the following formula [I] or a salt thereof,

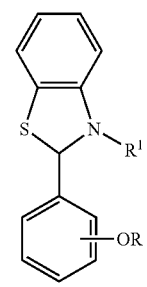

[I]

wherein R is an alkyl group having an amino group as a substituent; and $R^1$ is acyl.

2. A method of treating pain or pruritis comprising administering to a patient in need thereof a pharmaceutically effective amount of a κ opioid receptor agonist comprising a compound represented by the following formula [II] or a salt thereof,

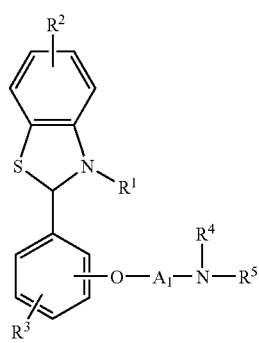

[II]

wherein R¹ is acyl;

R² and R³ are the same or different and are hydrogen, halogen, alkyl, cycloalkyl, aryl, hydroxyl or an ester thereof, alkoxy, aryloxy, carboxyl or an ester thereof, alkylcarbonyl, arylcarbonyl, amino, alkylamino, arylamino, cyano or nitro, wherein the alkyl, cycloalkyl, aryl, alkoxy, aryloxy, alkylcarbonyl, arylcarbonyl, alkylamino or arylamino are unsubstituted or substituted by halogen, alkyl, cycloalkyl, aryl, hydroxyl or an ester thereof, alkoxy, aryloxy, carboxyl or an ester thereof, alkylcarbonyl, arylcarbonyl, amino, alkylamino, arylamino, cyano or nitro;

R⁴ and R⁵, are the same or different, and are hydrogen, alkyl, cycloalkyl, aryl, hydroxyl or an ester thereof, alkoxy, aryloxy or acyl, wherein the alkyl, cycloalkyl, aryl, alkoxy, aryloxy or acyl are unsubstituted or substituted by a substituent selected from the group consisting of halogen, alkyl, cycloalkyl, aryl, hydroxyl or an ester thereof, alkoxy, aryloxy, carboxyl or an ester thereof, alkylcarbonyl, arylcarbonyl, amino, alkylamino, arylamino, mercapto, alkylthio, arylthio, cyano, nitro and a heterocycle, and wherein the alkyl, cycloalkyl, aryl, alkoxy, aryloxy, alkylcarbonyl, arylcarbonyl, alkylamino, arylamino, alkylthio, arylthio or heterocycle substituent is unsubstituted or substituted by aryl, hydroxyl or an ester thereof, alkoxy, aryloxy, alkoxyalkoxy or carboxyl or an ester thereof; or R⁴ and R⁵ are bonded to each other to form an unsubstituted heterocycle or a heterocycle substituted by halogen, alkyl, cycloalkyl, aryl, hydroxyl or an ester thereof, alkoxy, aryloxy or carboxyl or an ester thereof, and wherein the alkyl, cycloalkyl, aryl, alkoxy or aryloxy are unsubstituted or substituted by aryl, hydroxyl or an ester thereof, alkoxy, aryloxy, alkoxyalkoxy or carboxyl or an ester thereof; and $A_1$ is alkylene.

3. The method as claimed in claim 2, wherein R² and R³ are the same or different and are hydrogen, halogen, alkoxy, unsubstituted alkyl or alkyl substituted by halogen.

4. The method as claimed in claim 2, wherein R⁴ and R⁵ are the same or different and are hydrogen, alkyl, cycloalkyl, hydroxyl or an ester thereof or alkoxy, wherein the alkyl is unsubstituted or substituted by a substituent selected from the group consisting of alkyl, cycloalkyl, aryl, hydroxyl or an ester thereof, alkoxy, carboxyl or an ester thereof, mercapto, alkylthio and a heterocycle, and wherein the alkyl or alkoxy substituent is unsubstituted or substituted by hydroxyl or an ester thereof, alkoxy or alkoxyalkoxy.

5. The method as claimed in claim 2, wherein R⁴ and R⁵ are bonded to each other to form a pyrrolidine ring or a piperidine ring, wherein the pyrrolidine ring or piperidine ring is unsubstituted or substituted by alkyl, hydroxyl or an ester thereof, alkoxy or carboxyl or an ester thereof, and wherein the alkyl is unsubstituted or substituted by hydroxyl or an ester thereof or alkoxy.

6. The method as claimed in claim 2, wherein
R¹ is acyl,
R² is hydrogen, halogen or alkyl, wherein the alkyl is unsubstituted or substituted by halogen,
R³ is halogen or alkoxy,
R⁴ is hydrogen, alkyl or cycloalkyl, wherein the alkyl is unsubstituted or substituted by a substituent selected from the group consisting of alkyl, cycloalkyl, aryl, hydroxyl or an ester thereof and alkoxy, and wherein the alkyl substituent is unsubstituted or substituted by hydroxyl or an ester thereof or alkoxy,
R⁵ is alkyl, hydroxyl or an ester thereof or alkoxy, wherein the alkyl is unsubstituted or substituted by a substituent selected from the group consisting of cycloalkyl, aryl, hydroxyl or an ester thereof, alkoxy, carboxyl or an ester thereof, mercapto, alkylthio and a heterocycle, and wherein the alkoxy substituent is unsubstituted or substituted by hydroxyl or an ester thereof, alkoxy or alkoxyalkoxy, or
R⁴ and R⁵ are bonded with each other to form a pyrrolidine ring or a piperidine ring, wherein the pyrrolidine ring or piperidine ring is unsubstituted or substituted by a substituent selected from the group consisting of alkyl, hydroxyl or an ester thereof, alkoxy and carboxyl or an ester thereof, and wherein the alkyl substituent is unsubstituted or substituted by hydroxyl or an ester thereof or alkoxy, and
$A_1$ is alkylene.

7. The method as claimed in claim 2, wherein
R¹ is acyl,
R² is hydrogen, halogen or alkyl, wherein the alkyl can be substituted by halogen,
R³ is halogen or alkoxy,
R⁴ is cycloalkyl or alkyl which is unsubstituted or substituted by alkyl, cycloalkyl, aryl, hydroxyl or an ester thereof or alkoxy,
R⁵ is alkyl, hydroxyl or an ester thereof or alkoxy, wherein the alkyl is unsubstituted or substituted by a substituent selected from the group consisting of hydroxyl or an ester thereof, alkoxy, mercapto or alkylthio, and wherein the alkoxy substituent is unsubstituted or substituted by alkoxy or alkoxyalkoxy, or
R⁴ and R⁵ are bonded to each other to form a pyrrolidine ring, wherein the pyrrolidine ring is unsubstituted or substituted by alkyl, hydroxyl or an ester thereof or alkoxy, and the alkyl is unsubstituted or substituted by hydroxyl or an ester thereof or alkoxy, and
$A_1$ is alkylene.

8. The method as claimed in claim 1, wherein the method is for treating pain caused by a rheumatic disease.

9. The method as claimed in claim 2, wherein the method is for treating pain caused by a rheumatic disease.

10. The method as claimed in claim 3, wherein the method is for treating pain caused by a rheumatic disease.

11. The method as claimed in claim 4, wherein the method is for treating pain caused by a rheumatic disease.

12. The method as claimed in claim 5, wherein the method is for treating pain caused by a rheumatic disease.

13. The method as claimed in claim 6, wherein the method is for treating pain caused by a rheumatic disease.

14. The method as claimed in claim 7, wherein the method is for treating pain caused by a rheumatic disease.

* * * * *